(12) United States Patent
Adams et al.

(10) Patent No.: US 9,392,935 B2
(45) Date of Patent: Jul. 19, 2016

(54) METHODS FOR PERFORMING A MEDICAL PROCEDURE

(75) Inventors: Ronald D. Adams, Holliston, MA (US); William H. Gruber, Southborough, MA (US); David L. Foshee, Apex, NC (US); Theodore J. Mosler, Raleigh, NC (US); Douglas R. Drew, Raleigh, NC (US)

(73) Assignee: HOLOGIC, Inc., Marlborough, MA (US)

( * ) Notice: Subject to any disclaimer, the term of this patent is extended or adjusted under 35 U.S.C. 154(b) by 2695 days.

(21) Appl. No.: 11/923,482

(22) Filed: Oct. 24, 2007

(65) Prior Publication Data

US 2008/0146873 A1     Jun. 19, 2008

Related U.S. Application Data

(60) Provisional application No. 60/857,440, filed on Nov. 7, 2006, provisional application No. 60/910,618, filed on Apr. 6, 2007, provisional application No. 60/910,625, filed on Apr. 6, 2007.

(51) Int. Cl.
*A61B 1/00*     (2006.01)
*A61B 1/303*     (2006.01)
(Continued)

(52) U.S. Cl.
CPC ............. *A61B 1/303* (2013.01); *A61B 17/0218* (2013.01); *A61B 17/42* (2013.01);
(Continued)

(58) Field of Classification Search
USPC ......... 600/104, 105, 115, 116, 153, 156, 158, 600/201, 204, 215, 221, 229
See application file for complete search history.

(56) References Cited

U.S. PATENT DOCUMENTS

| 2,849,002 A | 8/1958 | Oddo et al. |
| 3,561,429 A | 2/1971 | Jewett |

(Continued)

FOREIGN PATENT DOCUMENTS

| EP | 0010650 | 5/1980 |
| EP | 0044877 | 2/1982 |

(Continued)

OTHER PUBLICATIONS

International Search Report and Written Opinion Received in PCT/US07/83982 Dated May 20, 2008.

(Continued)

*Primary Examiner* — Anhtuan T Nguyen
*Assistant Examiner* — Timothy J Neal
(74) *Attorney, Agent, or Firm* — Vista IP Law Group LLP

(57) ABSTRACT

Methods are disclosed, for performing therapeutic or diagnostic procedures at a remote site. According to one embodiment, the methods include the use of a system including an introducer designed for transcervical insertion into the uterus. The introducer is constructed to include a fluid lumen, an instrument lumen, and a visualization lumen. The system may include a fluid source, which is coupled to the fluid lumen and is used to deliver a fluid to the uterus either for washing the uterus or for fluid distension of the uterus. The system additionally includes a tissue modifying device, such as a morcellator, and a distension device for distending the uterus and/or for maintaining the uterus in a distended state. The tissue modifying device and the distension device are alternately deliverable to the uterus through the instrument lumen. The system may further include a hysteroscope deliverable to the uterus through the visualization lumen.

15 Claims, 19 Drawing Sheets

(51) Int. Cl.
    *A61B 17/02*    (2006.01)
    *A61B 17/42*    (2006.01)
    *A61M 25/00*    (2006.01)
    *A61B 1/12*         (2006.01)
    *A61B 17/00*        (2006.01)
    *A61B 17/22*        (2006.01)
    *A61B 17/3207*      (2006.01)
    *A61B 17/34*        (2006.01)

(52) U.S. Cl.
    CPC ....... *A61M25/0023* (2013.01); *A61M 25/0097* (2013.01); *A61B 1/00135* (2013.01); *A61B 2017/00867* (2013.01); *A61B 2017/22069* (2013.01); *A61B 2017/320775* (2013.01); *A61B 2017/3445* (2013.01); *A61B 2017/4216* (2013.01)

(56) References Cited

U.S. PATENT DOCUMENTS

| | | |
|---|---|---|
| 4,188,952 A | 2/1980 | Loschilov et al. |
| 4,198,981 A | 4/1980 | Sinnreich |
| 4,203,444 A | 5/1980 | Bonnell et al. |
| 4,246,902 A | 1/1981 | Martinez |
| 4,261,360 A | 4/1981 | Perez |
| 4,598,698 A | 7/1986 | Siegmund |
| 4,598,710 A | 7/1986 | Klienberg et al. |
| 4,650,462 A | 3/1987 | DeSatnick et al. |
| 4,673,393 A | 6/1987 | Suzuki et al. |
| 4,700,694 A | 10/1987 | Shishido |
| 4,729,763 A | 3/1988 | Henrie |
| 4,848,323 A * | 7/1989 | Marijnissen et al. ......... 600/108 |
| 4,895,565 A | 1/1990 | Hillstead |
| 4,949,718 A | 8/1990 | Neuwirth et al. |
| 4,998,527 A | 3/1991 | Meyer |
| 5,078,725 A | 1/1992 | Enderle et al. |
| 5,104,377 A | 4/1992 | Levine |
| 5,108,414 A | 4/1992 | Enderle et al. |
| 5,125,903 A | 6/1992 | McLaughlin et al. |
| 5,163,433 A | 11/1992 | Kagawa et al. |
| 5,163,949 A | 11/1992 | Bonutti |
| 5,183,031 A | 2/1993 | Rossoff |
| 5,195,541 A | 3/1993 | Obenchain |
| 5,201,756 A | 4/1993 | Horzewski et al. |
| 5,222,971 A | 6/1993 | Willard et al. |
| 5,246,016 A | 9/1993 | Lieber et al. |
| 5,259,836 A | 11/1993 | Thurmond et al. |
| 5,269,798 A | 12/1993 | Winkler |
| 5,275,609 A | 1/1994 | Pingleton et al. |
| 5,304,115 A | 4/1994 | Pflueger et al. |
| 5,320,091 A | 6/1994 | Grossi et al. |
| 5,334,183 A | 8/1994 | Wuchinich |
| 5,361,752 A | 11/1994 | Moll et al. |
| 5,377,668 A | 1/1995 | Ehmsen et al. |
| 5,392,765 A | 2/1995 | Muller |
| 5,402,772 A | 4/1995 | Moll et al. |
| 5,423,844 A | 6/1995 | Miller |
| 5,443,470 A | 8/1995 | Stern et al. |
| 5,450,843 A | 9/1995 | Moll et al. |
| 5,458,112 A | 10/1995 | Weaver |
| 5,484,401 A | 1/1996 | Rodriguez et al. |
| 5,503,626 A | 4/1996 | Goldrath |
| 5,505,730 A | 4/1996 | Edwards |
| 5,514,091 A | 5/1996 | Yoon |
| 5,522,790 A | 6/1996 | Moll et al. |
| 5,540,658 A | 7/1996 | Evans et al. |
| 5,575,788 A | 11/1996 | Baker et al. |
| 5,601,583 A | 2/1997 | Donahue et al. |
| 5,602,449 A | 2/1997 | Krause et al. |
| 5,618,296 A | 4/1997 | Sorensen et al. |
| 5,624,395 A | 4/1997 | Mikhail et al. |
| 5,624,399 A | 4/1997 | Ackerman |
| 5,656,013 A | 8/1997 | Yoon |
| 5,695,511 A | 12/1997 | Cano et al. |
| 5,697,940 A | 12/1997 | Chu et al. |
| 5,709,664 A | 1/1998 | Vandenbroek et al. |
| 5,725,525 A | 3/1998 | Kordis |
| 5,730,725 A | 3/1998 | Yoon |
| 5,738,629 A | 4/1998 | Moll et al. |
| 5,741,287 A | 4/1998 | Alden et al. |
| 5,743,850 A | 4/1998 | Moll et al. |
| 5,743,851 A | 4/1998 | Moll et al. |
| 5,749,845 A | 5/1998 | Hildebrand et al. |
| 5,749,889 A | 5/1998 | Bacich et al. |
| 5,755,731 A | 5/1998 | Grinberg |
| 5,782,800 A | 7/1998 | Yoon |
| 5,800,493 A | 9/1998 | Stevens et al. |
| 5,807,401 A | 9/1998 | Grieshaber et al. |
| 5,823,945 A | 10/1998 | Moll et al. |
| 5,843,046 A | 12/1998 | Motisi et al. |
| 5,855,549 A | 1/1999 | Newman |
| 5,857,585 A | 1/1999 | Tolkoff et al. |
| 5,865,728 A | 2/1999 | Moll et al. |
| 5,873,815 A | 2/1999 | Kerin et al. |
| 5,891,134 A | 4/1999 | Goble et al. |
| 5,899,915 A | 5/1999 | Saadat |
| 5,902,251 A | 5/1999 | vanHooydonk |
| 5,904,649 A | 5/1999 | Andrese |
| 5,904,680 A | 5/1999 | Kordis et al. |
| 5,911,739 A | 6/1999 | Kordis et al. |
| 5,916,198 A | 6/1999 | Dillow |
| 5,954,714 A | 9/1999 | Saadat et al. |
| 5,954,715 A | 9/1999 | Harrington et al. |
| 5,961,444 A | 10/1999 | Thompson |
| 5,961,532 A | 10/1999 | Finley et al. |
| 5,964,755 A | 10/1999 | Edwards |
| 5,964,777 A | 10/1999 | Drucker |
| 5,972,000 A | 10/1999 | Beyar et al. |
| 6,002,968 A | 12/1999 | Edwards |
| 6,032,673 A | 3/2000 | Savage et al. |
| 6,039,748 A | 3/2000 | Savage et al. |
| 6,042,590 A | 3/2000 | Sporri et al. |
| 6,068,626 A | 5/2000 | Harrington et al. |
| 6,080,129 A | 6/2000 | Blaisdell |
| 6,086,544 A | 7/2000 | Hibner et al. |
| 6,117,070 A | 9/2000 | Akiba |
| 6,126,635 A | 10/2000 | Simpson et al. |
| 6,139,570 A | 10/2000 | Saadat et al. |
| 6,149,632 A | 11/2000 | Landuyt |
| 6,159,209 A | 12/2000 | Hakky |
| 6,187,346 B1 * | 2/2001 | Neuwirth ...................... 424/618 |
| 6,190,357 B1 | 2/2001 | Ferrarl et al. |
| 6,216,043 B1 | 4/2001 | Swanson et al. |
| 6,216,044 B1 | 4/2001 | Kordis |
| 6,221,007 B1 | 4/2001 | Green |
| 6,234,958 B1 * | 5/2001 | Snoke et al. .................. 600/114 |
| 6,293,952 B1 | 9/2001 | Brosens et al. |
| 6,319,272 B1 | 11/2001 | Brenneman et al. |
| 6,328,686 B1 | 12/2001 | Kovac |
| 6,378,524 B1 | 4/2002 | Jones |
| 6,387,110 B1 | 5/2002 | Drucker et al. |
| 6,395,012 B1 | 5/2002 | Yoon et al. |
| 6,428,498 B2 | 8/2002 | Uflacker |
| 6,428,539 B1 | 8/2002 | Baxter et al. |
| 6,432,116 B1 | 8/2002 | Callister et al. |
| 6,440,061 B1 | 8/2002 | Wenner et al. |
| 6,458,076 B1 | 10/2002 | Pruitt |
| 6,471,644 B1 | 10/2002 | Sidor, Jr. |
| 6,494,909 B2 | 12/2002 | Greenhalgh |
| 6,537,207 B1 | 3/2003 | Rice et al. |
| 6,547,784 B1 | 4/2003 | Thompson et al. |
| 6,565,557 B1 | 5/2003 | Sporri et al. |
| 6,605,037 B1 | 8/2003 | Moll et al. |
| 6,607,545 B2 | 8/2003 | Kammerer et al. |
| 6,612,977 B2 | 9/2003 | Staskin et al. |
| 6,626,940 B2 | 9/2003 | Crowley |
| 6,638,235 B2 | 10/2003 | Miller et al. |
| 6,673,101 B1 | 1/2004 | Fitzgerald et al. |
| 6,682,477 B2 | 1/2004 | Boebel et al. |
| 6,709,667 B1 | 3/2004 | Lowe et al. |
| 6,742,236 B1 | 6/2004 | Dion et al. |
| 6,743,184 B2 * | 6/2004 | Sampson et al. ............. 600/560 |
| 6,763,833 B1 | 7/2004 | Khera et al. |

(56) References Cited

U.S. PATENT DOCUMENTS

| | | |
|---|---|---|
| 6,802,825 B2 | 10/2004 | Ackerman et al. |
| 6,805,131 B2 | 10/2004 | Kordis |
| 6,812,204 B1 | 11/2004 | McHale et al. |
| 6,821,274 B2 | 11/2004 | McHale et al. |
| 6,827,703 B1 | 12/2004 | Ackerman |
| 6,858,024 B1 | 2/2005 | Berg et al. |
| 6,896,682 B1 | 5/2005 | Mcclellan et al. |
| 6,951,569 B2 | 10/2005 | Nohilly et al. |
| 6,960,203 B2 | 11/2005 | Xiao et al. |
| 6,979,332 B2 | 12/2005 | Adams |
| 6,997,925 B2 | 2/2006 | Maguire et al. |
| 7,037,321 B2 | 5/2006 | Sachdeva et al. |
| 7,070,559 B2 | 7/2006 | Adams et al. |
| 7,105,003 B2 | 9/2006 | Hiltebrandt |
| 7,150,713 B2 | 12/2006 | Shener et al. |
| 7,189,206 B2 | 3/2007 | Quick et al. |
| 7,226,459 B2 | 6/2007 | Cesarini et al. |
| 7,226,460 B2 | 6/2007 | Gibson et al. |
| 7,249,602 B1 | 7/2007 | Emanuel |
| 7,458,940 B2 | 12/2008 | Miller |
| 7,462,187 B2 | 12/2008 | Johnston et al. |
| 7,468,060 B2 | 12/2008 | Utley et al. |
| 7,481,817 B2 | 1/2009 | Sauer |
| 7,491,212 B2 | 2/2009 | Sikora et al. |
| 7,497,833 B2 | 3/2009 | Miller |
| 7,510,563 B2 | 3/2009 | Cesarini et al. |
| 7,588,545 B2 | 9/2009 | Cohen et al. |
| 7,611,474 B2 | 11/2009 | Hibner et al. |
| 7,666,200 B2 | 2/2010 | Heisler |
| 7,749,254 B2 | 7/2010 | Sobelman et al. |
| 7,753,857 B2 | 7/2010 | Hibner |
| 7,763,033 B2 | 7/2010 | Gruber et al. |
| 7,785,250 B2 | 8/2010 | Nakao |
| 7,806,835 B2 | 10/2010 | Hibner et al. |
| 7,938,804 B2 | 5/2011 | Fischvogt |
| 2001/0008575 A1 | 7/2001 | Rho et al. |
| 2001/0029371 A1 | 10/2001 | Kordis |
| 2001/0041900 A1 | 11/2001 | Callister et al. |
| 2001/0047183 A1 | 11/2001 | Privitera et al. |
| 2001/0056222 A1 | 12/2001 | Rudischhauser et al. |
| 2002/0010457 A1 | 1/2002 | Duchon et al. |
| 2002/0013601 A1 | 1/2002 | Nobles et al. |
| 2002/0020417 A1 | 2/2002 | Nikolchev |
| 2002/0068934 A1 | 6/2002 | Edwards et al. |
| 2002/0082634 A1 | 6/2002 | Kammerer et al. |
| 2003/0032953 A1* | 2/2003 | VanDusseldorp et al. ...... 606/41 |
| 2003/0050639 A1 | 3/2003 | Yachia et al. |
| 2003/0083684 A1 | 5/2003 | Cesarini et al. |
| 2003/0114875 A1 | 6/2003 | Sjostrom |
| 2003/0153940 A1 | 8/2003 | Nohilly et al. |
| 2004/0002702 A1 | 1/2004 | Xiao et al. |
| 2004/0002703 A1 | 1/2004 | Xiao et al. |
| 2004/0049211 A1 | 3/2004 | Tremulis et al. |
| 2004/0116955 A1 | 6/2004 | Foltz et al. |
| 2004/0127932 A1 | 7/2004 | Shah |
| 2004/0204682 A1 | 10/2004 | Smith |
| 2004/0225187 A1 | 11/2004 | Kamrava et al. |
| 2004/0255957 A1 | 12/2004 | Cafferata |
| 2004/0267157 A1 | 12/2004 | Miller et al. |
| 2005/0027245 A1 | 2/2005 | Sachdeva et al. |
| 2005/0045183 A1 | 3/2005 | Callister et al. |
| 2005/0080318 A1 | 4/2005 | Squicciarini |
| 2005/0090849 A1 | 4/2005 | Adams |
| 2005/0107663 A1 | 5/2005 | Saadat et al. |
| 2005/0113715 A1 | 5/2005 | Schwindt et al. |
| 2005/0113836 A1 | 5/2005 | Lozier et al. |
| 2005/0113857 A1 | 5/2005 | Nohilly et al. |
| 2005/0177168 A1 | 8/2005 | Brunnett et al. |
| 2005/0182397 A1 | 8/2005 | Ryan |
| 2005/0222598 A1 | 10/2005 | Ho et al. |
| 2005/0234437 A1 | 10/2005 | Baxter et al. |
| 2005/0240206 A1 | 10/2005 | Sjostrom |
| 2005/0245960 A1 | 11/2005 | Grundeman |
| 2005/0250933 A1 | 11/2005 | Binz et al. |
| 2005/0250993 A1 | 11/2005 | Jaeger |
| 2005/0267408 A1 | 12/2005 | Grandt et al. |
| 2005/0277970 A1 | 12/2005 | Norman et al. |
| 2005/0277975 A1 | 12/2005 | Saadat et al. |
| 2005/0288551 A1 | 12/2005 | Callister et al. |
| 2006/0004436 A1 | 1/2006 | Amarant et al. |
| 2006/0009798 A1 | 1/2006 | Callister et al. |
| 2006/0036138 A1 | 2/2006 | Heller et al. |
| 2006/0047185 A1 | 3/2006 | Sherner et al. |
| 2006/0064074 A1 | 3/2006 | Mallaby |
| 2006/0089658 A1 | 4/2006 | Harrington |
| 2006/0189972 A1 | 8/2006 | Grossman |
| 2006/0200042 A1 | 9/2006 | Weikel, Jr. et al. |
| 2006/0206136 A1 | 9/2006 | Sachdeva et al. |
| 2006/0212055 A1 | 9/2006 | Karabey et al. |
| 2006/0229647 A1 | 10/2006 | Spitz et al. |
| 2006/0241344 A1 | 10/2006 | Wilk |
| 2006/0241586 A1 | 10/2006 | Wilk |
| 2006/0241630 A1 | 10/2006 | Brunnett et al. |
| 2006/0293560 A1 | 12/2006 | Nguyen et al. |
| 2007/0010845 A1 | 1/2007 | Gong et al. |
| 2007/0161957 A1 | 7/2007 | Guenther et al. |
| 2007/0225744 A1 | 9/2007 | Nobles et al. |
| 2007/0227544 A1 | 10/2007 | Swann et al. |
| 2007/0232859 A1 | 10/2007 | Secrest et al. |
| 2008/0015621 A1 | 1/2008 | Emanuel |
| 2008/0051758 A1 | 2/2008 | Rioux et al. |
| 2008/0058588 A1 | 3/2008 | Emanuel |
| 2008/0058595 A1 | 3/2008 | Snoke et al. |
| 2008/0065125 A1 | 3/2008 | Olson |
| 2008/0147012 A1 | 6/2008 | Rome |
| 2008/0183192 A1 | 7/2008 | Saal et al. |
| 2008/0234715 A1 | 9/2008 | Pesce et al. |
| 2008/0245371 A1 | 10/2008 | Gruber et al. |
| 2008/0249366 A1 | 10/2008 | Gruber et al. |
| 2008/0249553 A1 | 10/2008 | Gruber et al. |
| 2008/0262302 A1 | 10/2008 | Azarbarzin et al. |
| 2008/0281224 A1 | 11/2008 | Johnson |
| 2008/0319342 A1 | 12/2008 | Shabaz et al. |
| 2009/0005739 A1 | 1/2009 | Hart et al. |
| 2009/0048485 A1 | 2/2009 | Heisler |
| 2009/0054728 A1 | 2/2009 | Trusty |
| 2009/0118699 A1 | 5/2009 | Utley et al. |
| 2009/0137927 A1 | 5/2009 | Miller |
| 2009/0177217 A1 | 7/2009 | Keller |
| 2009/0198149 A1 | 8/2009 | Privitera et al. |
| 2009/0270895 A1 | 10/2009 | Churchill et al. |
| 2009/0270896 A1 | 10/2009 | Sullivan et al. |
| 2009/0270897 A1 | 10/2009 | Adams et al. |
| 2009/0270898 A1 | 10/2009 | Chin et al. |
| 2010/0063360 A1 | 3/2010 | Harrington et al. |
| 2010/0087798 A1 | 4/2010 | Adams et al. |
| 2010/0152533 A1 | 6/2010 | Mark |
| 2010/0152758 A1 | 6/2010 | Mark et al. |
| 2010/0152761 A1 | 6/2010 | Mark |
| 2010/0160818 A1 | 6/2010 | Haberstich et al. |
| 2010/0179480 A1 | 7/2010 | Sugiki et al. |
| 2010/0185153 A1 | 7/2010 | Sugiki et al. |
| 2010/0198242 A1 | 8/2010 | Heisler |
| 2010/0274194 A1 | 10/2010 | Sobelman et al. |
| 2010/0312053 A1 | 12/2010 | Larsen |
| 2011/0034943 A1 | 2/2011 | Churchill et al. |
| 2011/0054488 A1 | 3/2011 | Gruber et al. |
| 2011/0077674 A1 | 3/2011 | Sullivan et al. |
| 2011/0118544 A1 | 5/2011 | Adams et al. |

FOREIGN PATENT DOCUMENTS

| | | |
|---|---|---|
| EP | 0141589 | 5/1985 |
| EP | 0366292 | 5/1990 |
| EP | 0449663 | 10/1991 |
| EP | 0531710 | 10/1991 |
| EP | 0539125 | 4/1993 |
| EP | 782427 | 2/1996 |
| EP | 853468 | 5/1996 |
| EP | 0812573 | 12/1997 |
| EP | 1259180 | 9/2001 |
| EP | 1635695 | 1/2005 |
| FR | 2701401 | 8/1994 |
| WO | WO 94/07445 | 4/1994 |

(56) References Cited

FOREIGN PATENT DOCUMENTS

| | | |
|---|---|---|
| WO | WO 94/11052 | 5/1994 |
| WO | WO 95/10326 | 4/1995 |
| WO | WO 95/32011 | 11/1995 |
| WO | WO 96/15741 | 5/1996 |
| WO | WO 98/18520 | 5/1998 |
| WO | WO 98/29068 | 7/1998 |
| WO | WO 98/51244 | 11/1998 |
| WO | WO 99/60960 | 12/1999 |
| WO | WO 00/00100 | 1/2000 |
| WO | WO 00/12832 | 3/2000 |
| WO | WO 00/66031 | 11/2000 |
| WO | WO 01/08575 | 2/2001 |
| WO | WO 03/037194 | 5/2003 |
| WO | WO 2005/009504 | 2/2005 |
| WO | WO 2005/048862 | 6/2005 |
| WO | WO 2005/074844 | 8/2005 |
| WO | WO 2005/104966 | 11/2005 |
| WO | WO 2009/111717 | 9/2009 |
| WO | WO 2010/127171 | 11/2010 |
| WO | WO 2010/127174 | 11/2010 |

OTHER PUBLICATIONS

International Search Report and Written Opinion Received in PCT/US08/59493 Dated Apr. 4, 2008.
International Search Report and Written Opinion Received in PCT/US07/83833 Dated Jun. 5, 2008.
International Search Report and Written Opinion Received in PCT/US08/59504 Dated Sep. 4, 2008.
International Search Report and Written Opinion Received in PCT/US08/59503 Dated Sep. 5, 2008.
U.S. Appl. No. 11/852,151, including its prosecution history, and the Office Actions, Gruber, et al.
U.S. Appl. No. 11/936,003, including its prosecution history, and the Office Actions, Gruber, et al.
U.S. Appl. No. 11/951,853, including its prosecution history, and the Office Actions, Gruber, et al.
U.S. Appl. No. 11/852,116, including its prosecution history, and the Office Actions, Gruber, et al.
U.S. Appl. No. 11/852,142, including its prosecution history, and the Office Actions, Gruber, et al.
U.S. Appl. No. 11/852,121, including its prosecution history, and the Office Actions, Adams, et al.
U.S. Appl. No. 11/852,200, including its prosecution history, and the Office Actions, Gruber, et al.
U.S. Appl. No. 11/923,357, including its prosecution history, and the Office Actions, Gruber, et al.
International Search Report Received and Written Opinion in PCT/US07/79449 Dated Jan. 28, 2008.
International Search Report and Written Opinion dated Jan. 11, 2011, in PCT Application No. PCT/US10/56416 in 14 pages.
International Search Report and Written Opinion dated Jul. 6, 2010, PCT Application No. PCT/US2010/033047 in 13 pages.
International Search Report and Written Opinion dated Jun. 29, 2010, PCT Application No. PCT/US2010/033050 in 7 pages.
"When mechanical dilation is necessary, a few prerequisites can make a difference", OBG Management, Apr. 2009, vol. 21, No. 4, p. 29-33.
Mark H. Emanuel, "The Intra Uterine Morcellator: A New Hysteroscopic Operating Technique to Remove Intrauterine Polyps and Myomas," Journal of Minimally Invasive Gynecology, vol. 12, p. 62-66 (2005).
U.S. Appl. No. 12/432,691, including its prosecution history, and the Office Actions, Adams, et al.
U.S. Appl. No. 12/432,702, including its prosecution history, and the Office Actions, Chin, et al.
U.S. Appl. No. 12/432,686, including its prosecution history, and the Office Actions, Sullivan, et al.
U.S. Appl. No. 12/432,675, including its prosecution history, and the Office Actions, Churchill, et al.
U.S. Appl. No. 12/432,647, including its prosecution history, and the Office Actions, Litscher, et al.

* cited by examiner

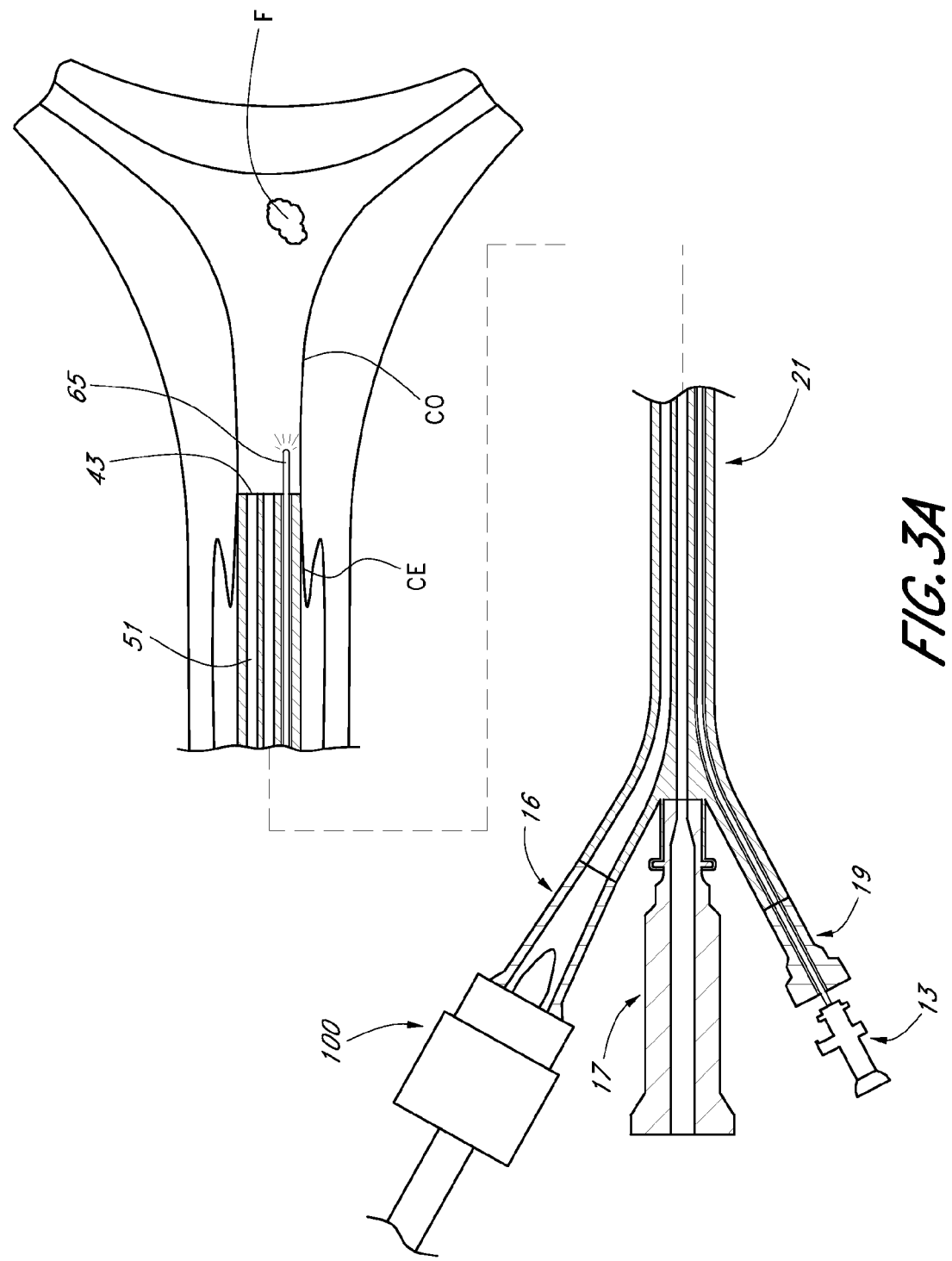

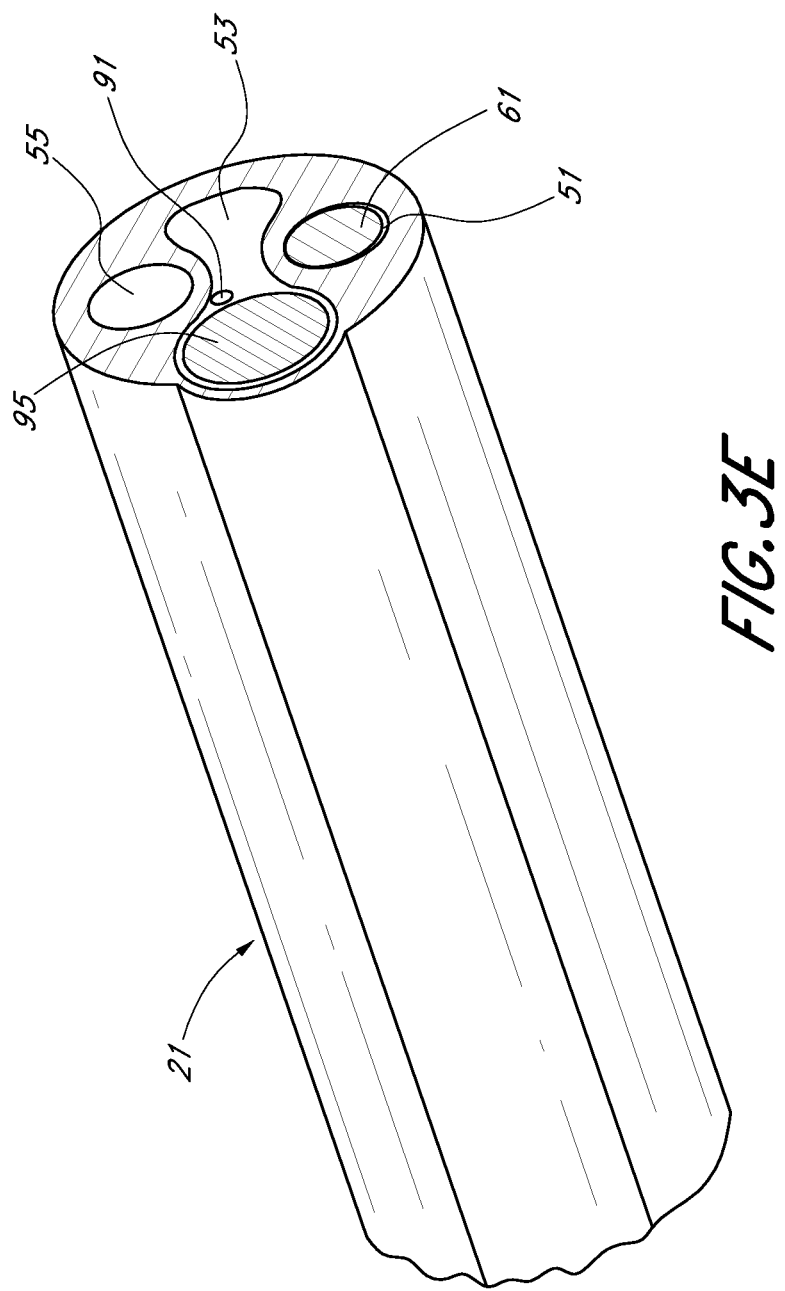

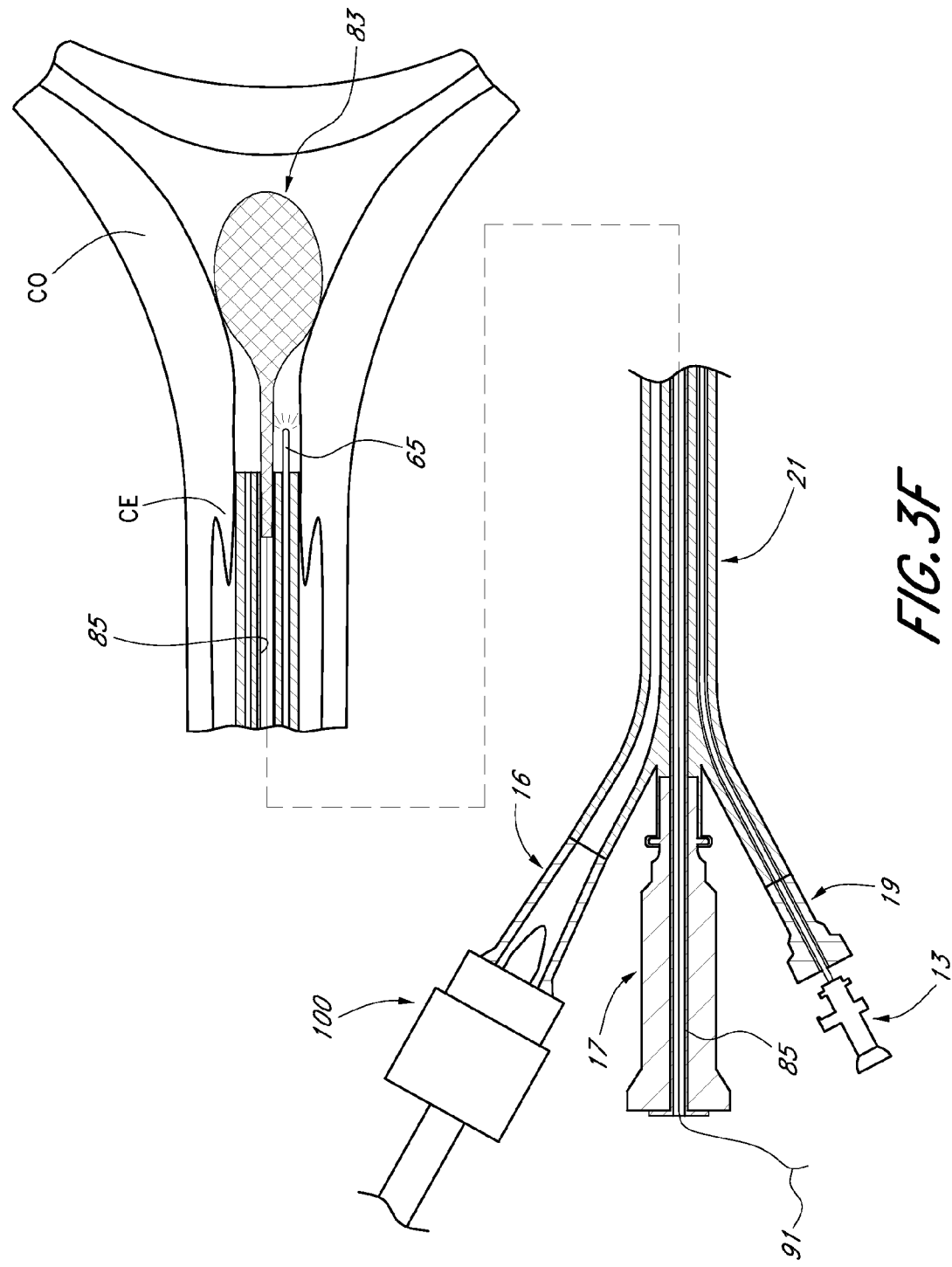

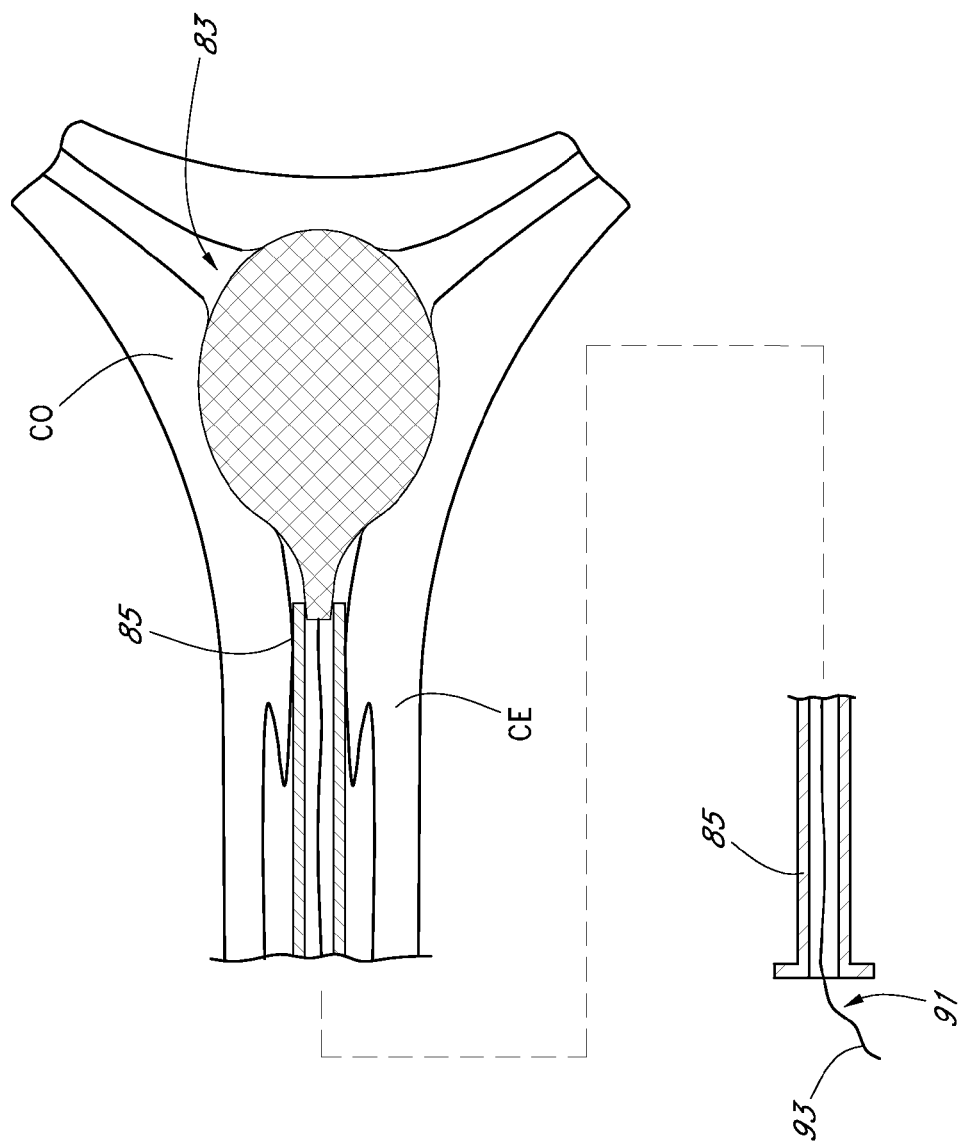

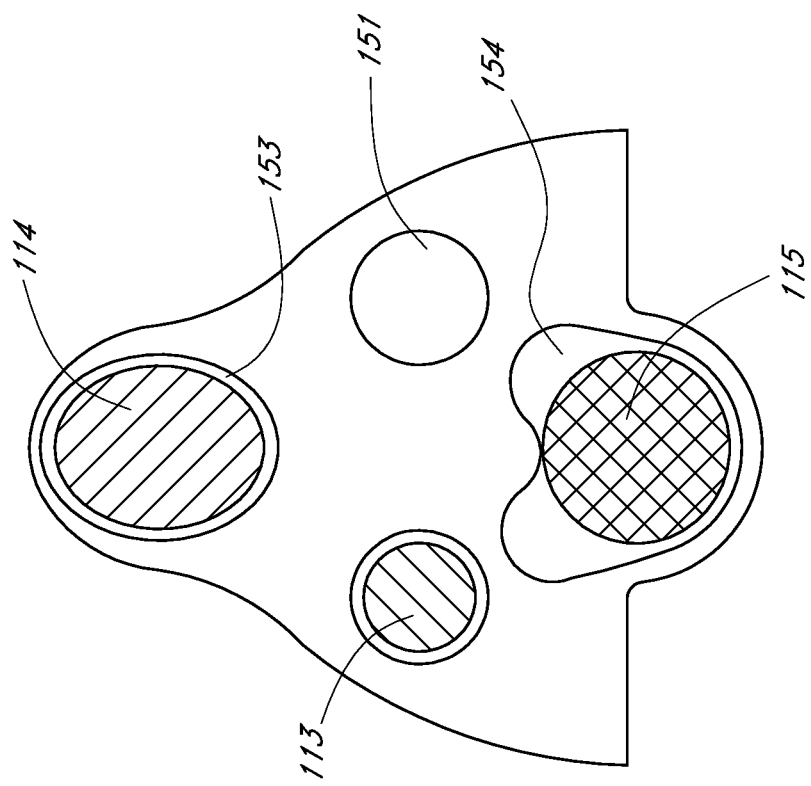

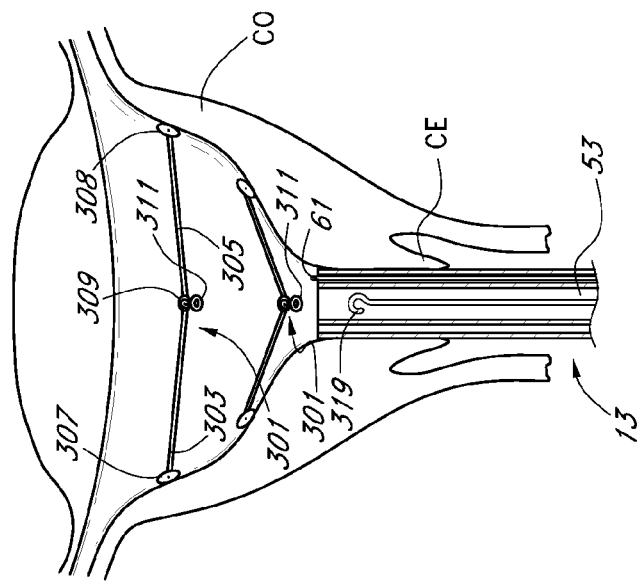
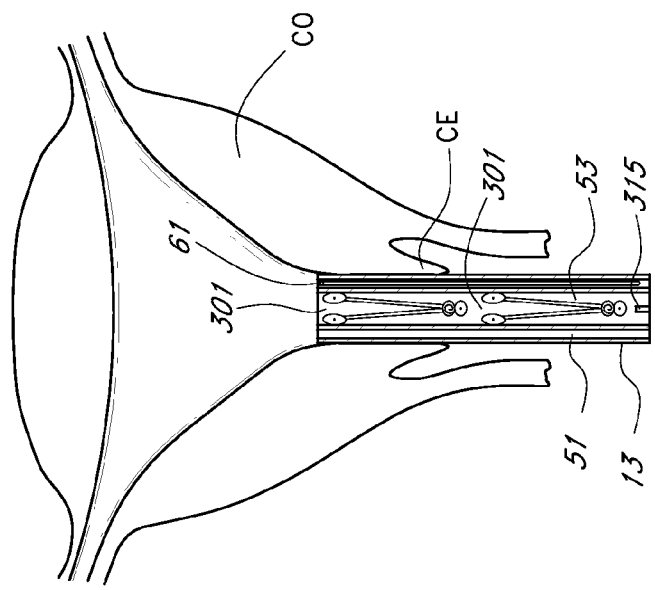
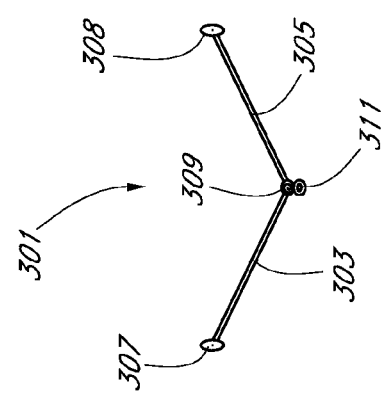

METHODS FOR PERFORMING A MEDICAL PROCEDURE

CROSS-REFERENCE TO RELATED APPLICATIONS

The present application claims the benefit under 35 U.S.C. 119(e) of U.S. Provisional Patent Application Ser. No. 60/857,440, filed Nov. 7, 2006, U.S. Provisional Patent Application Ser. No. 60/910,618, filed Apr. 6, 2007, and U.S. Provisional Patent Application Ser. No. 60/910,625, filed Apr. 6, 2007, all of which are incorporated herein by reference.

BACKGROUND OF THE INVENTION

The present invention relates generally to methods and systems for performing medical procedures and relates more particularly to a new method and system for performing a medical procedure.

There are many types of situations in which it is desirable for a medical procedure to be performed on a patient. Such a procedure may be diagnostic and/or therapeutic in nature. For example, in the field of gynecology, one may wish to examine and/or treat a uterus for various abnormal conditions including, but not limited to, the presence of fibroids, polyps, tumors, adhesions, or other abnormalities within a uterus; endometriosis or other abnormal bleeding; uterine prolapse; ectopic pregnancy; and fertility issues (both the inability to conceive and the desire to avoid pregnancy).

The uterus is a pear-shaped organ made up two distinct anatomical regions: the cervix and the corpus. The cervix is a narrow cylindrical passage (about 1.5-4.0 mm in diameter) which connects at its lower end with the vagina. The corpus, which is the portion of the uterus that grows during pregnancy to carry a fetus, is shaped to include two portions: the lower uterine segment and the fundus. The cervix widens at its upper end to form the lower uterine segment of the corpus. The lower uterine segment, in turn, widens at its upper end into the fundus of the corpus. Dimensionally, the length of the uterus, measured from the cervix to the fundus, is approximately 8-10 cm, and the maximum width of the uterus, which is near the fundus, is about 4-5 cm. Extending from the fundus of the uterus on either side are fallopian tubes. The fallopian tubes are continuous with the uterine cavity and allow the passage of an egg from an ovary to the uterus where the egg may implant if fertilized.

To facilitate the examination and/or treatment of the uterus, there should be ample space within the uterus. Unfortunately, however, adequate space typically does not exist naturally in the uterus because the uterus is a flaccid organ. As such, the walls of the uterus are typically in contact with one another when in a relaxed state. Consequently, active steps need to be taken to create a working space within the uterus.

The conventional technique for creating such a working space within the uterus is to administer a fluid to the uterus, transcervically, under sufficient pressure to cause the uterus to become distended. Examples of the fluid used conventionally to distend the uterus include gases like carbon dioxide and liquids like water or certain aqueous solutions (e.g., a saline solution or a sugar-based aqueous solution).

With the uterus thus distended, examination of the uterus is typically performed using a hysteroscope—a visualization device that is inserted transcervically into the uterus. If fibroids (i.e., benign tumors), polyps or other abnormalities are detected, such abnormalities may be removed, for example, by resection. Certain devices include the combination of visualization means, such as a hysteroscope, and resection means, such as a morcellator. Examples of such devices are disclosed in U.S. Pat. No. 6,032,673, inventor Savage et al., issued Mar. 7, 2000; U.S. Pat. No. 5,730,752, inventors Alden et al., issued Mar. 24, 1998; and PCT International Publication Number WO 99/11184, published Mar. 11, 1999.

Although the above-described technique of fluid distension is commonly practiced, there are certain shortcomings associated therewith. For example, because the distending fluid is administered under pressure (which pressure may be as great as 120 mm Hg or greater), there is a risk that such fluids may be taken up by a blood vessel in the uterus, i.e., intravasation, which uptake may be quite harmful to the patient. Because the risk of excess intravasation can lead to death, it is customary to monitor the fluid uptake on a continuous basis using a scale system. This risk of excess intravasation is particularly great when the fluid distension technique is followed by a procedure in which a blood vessel is cut, such as when abnormal or undesired tissue located in the uterus is resected.

Moreover, the above-described technique of fluid distension suffers from additional shortcomings. For example, throughout the entire period of time that the diagnostic and/or therapeutic procedure is performed, the distension fluid must be continuously administered under pressure to the patient to keep the uterus distended. This requires the availability of an adequate supply of the distending fluid. In addition, suitable equipment must be available to provide the requisite continuous flow of distending fluid to the patient. Furthermore, the above-described fluid distension technique may become messy, particularly when a liquid is used as the distension fluid, as some of the distension fluid within the uterus may escape proper collection and, instead, may leak from the patient to the surrounding environment.

For at least the above reasons, medical procedures involving fluid distension of the uterus are typically performed in a hospital and, as a result, bear a large cost due to the setting and the support personnel required.

SUMMARY OF THE INVENTION

The present invention provides a method and system as described below that may be used, for example, in the examination and/or treatment of the uterus.

Therefore, according to one aspect of the invention, there is provided a system for use in performing a medical procedure, the system comprising: an introducer for providing access to an internal site within a body; a mechanical expansion structure, the mechanical expansion structure being deliverable to the internal site using the introducer; a visualization device, the visualization device being deliverable to the internal site using the introducer; and a tissue modifying device, the tissue modifying device being deliverable to the internal site using the introducer.

According to another aspect of the invention, there is provided a method of performing a medical procedure, said method comprising the steps of using a mechanical expansion structure to distend a uterus or to maintain a distended uterus in a distended state; and performing at least one of examining and treating tissue located within the distended uterus.

According to yet another aspect of the invention, there is provided a method of performing a medical procedure, said method comprising the steps of inserting an introducer into a body to an internal site, the introducer including a visualization lumen and an instrument lumen; delivering a visualization device to the internal site through the visualization lumen; delivering a mechanical expansion structure to the internal site; deploying the mechanical expansion structure to distend the internal site; observing the distended internal site using the visualization device; delivering a tissue modifying device to the internal site through the instrument lumen; and modifying tissue at the internal site using the tissue modifying device.

Additional aspects, features and advantages, of the present invention will be set forth in part in the description which follows, and in part will be apparent from the description or may be learned by practice of the invention. In the description, reference is made to the accompanying drawings which form a part thereof and in which is shown by way of illustration various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. In the drawings wherein like reference numerals represent like parts:

FIGS. 3(a) through 3(f) are fragmentary, schematic views, partly in section, showing one way in which the system of FIG. 1 may be used to perform a medical procedure, such as the removal of a fibroid in a uterus;

FIGS. 4(a) through 4(d) are fragmentary, schematic views, partly in section, showing an alternate way in which the system of FIG. 1 may be used to perform a medical procedure, such as the removal of a fibroid in a uterus;

FIG. 10 is a transverse section view of the system shown in FIG. 6, with the hysteroscope, the morcellator and the distension mechanism being shown in simplified form;

FIG. 11 is a plan view of a mechanical expansion structure that may be used to maintain a uterus in a distended state, the mechanical expansion structure being constructed according to the teachings of the present invention; and FIGS. 12(a) and 12(b) are fragmentary schematic views, partly in section, illustrating one way in which the mechanical expansion structure of FIG. 11 may be used to maintain a uterus in a distended state.

DETAILED DESCRIPTION OF THE PREFERRED EMBODIMENT

Figure 1:
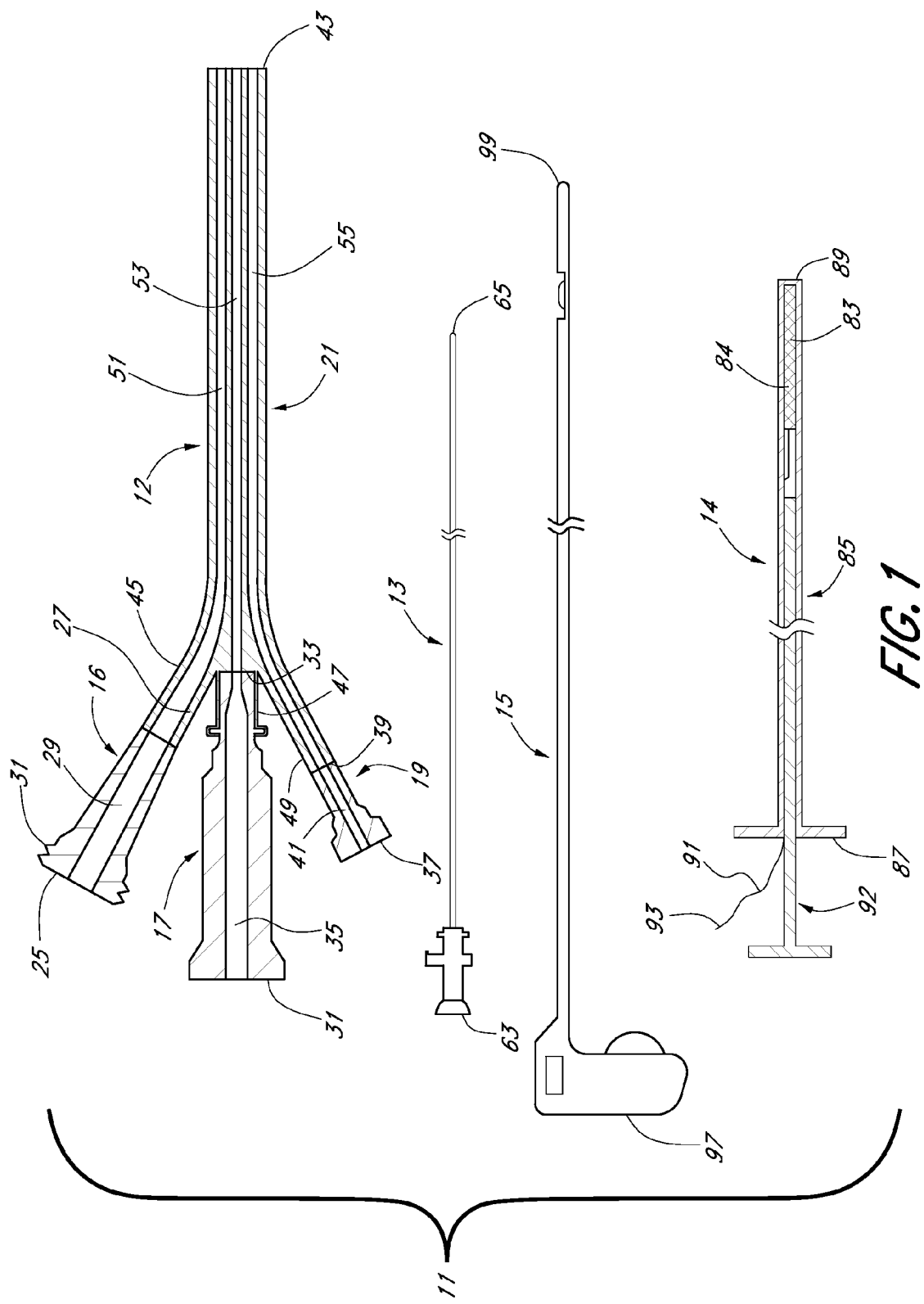
FIG. 1 is a plan view, partly in section, of a first embodiment of a system for use in accessing and in examining and/or treating a body cavity, the system being constructed according to the teachings of the present invention and being shown in a partially disassembled state.

Referring now to FIG. 1, there is shown a plan view, partly in section, of one embodiment of a system that may be used in accessing and in examining and/or treating a body cavity, the system being constructed according to the teachings of the present invention and being represented generally by reference numeral 11.

System 11, which is shown in a partially disassembled state, is particularly well-suited for use in accessing and examining and/or treating the uterus of a female patient. However, it should be understood that system 11 is not limited to such a use and may be used in other anatomies that may be apparent to those of ordinary skill in the art.

System 11 may comprise an introducer 12, a visualization device 13, a distension device 14 and a tissue modifying device 15. Introducer 12, in turn, may include a first port 16, a second port 17, a third port 19, and a flexible sheath 21. Ports 16, 17 and 19 are typically not intended for insertion into a patient whereas the distal end of sheath 21 is typically configured for insertion into a patient. A distal zone on sheath 21, configured to extend through and beyond the cervix typically has an OD of less than about 9 mm, typically less than about 8 mm and preferably less than about 7 mm (e.g., less than about 5.5 mm).

First port 16, which may be adapted to receive, for example, the distal end of a fluid-containing syringe (not shown) or other fluid source, may be shaped to include a proximal end 25, a distal end 27 and a longitudinal lumen 29. A helical thread or luer lock 31 may be provided on the exterior of port 16 near proximal end 25 to matingly engage a complementary thread or luer lock on a syringe or the like. Second port 17, which may be adapted to receive, for example, mechanical distension device 14, tissue modifying device 15, or another desired tool, may be shaped to include a proximal end 31, a distal end 33 and a longitudinal lumen 35. Third port 19, which may be adapted to receive, for example, visualization device 13, may be shaped to include a proximal end 37, a distal end 39 and a longitudinal lumen 41. Each of first port 16, second port 17, and third port 19 may be made of a rigid material, such as a rigid, medical grade plastic.

Figure 2:
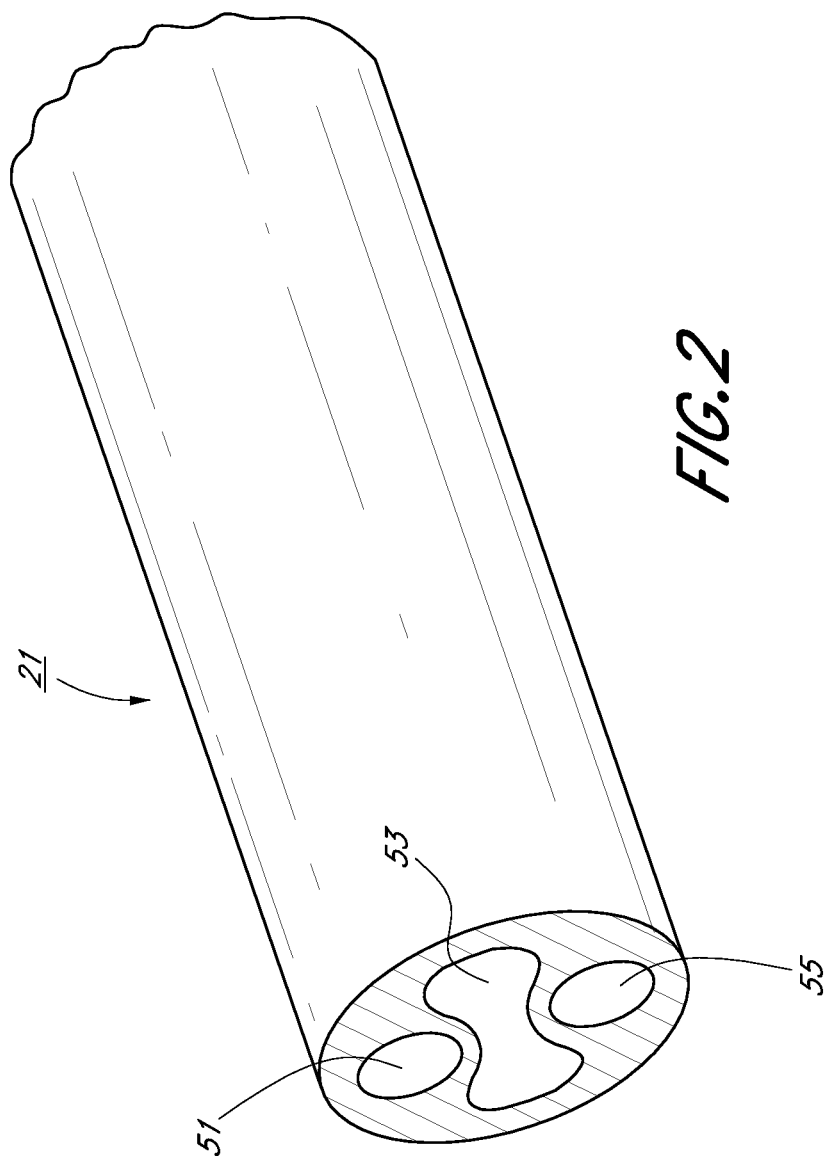
FIG. 2 is a fragmentary, perspective view, shown partly in section, of the introducer sheath shown in FIG. 1.

Sheath 21, which is also shown in FIG. 2, may be an elongated member made of an elastic or compliant or substantially noncompliant material, depending upon the desired radial expansion characteristic. Sheath 21 may be shaped to include a trifurcated proximal end and an unbranched distal end 43. The trifurcated proximal end of sheath 21 may include a first arm 45, a second arm 47 and a third arm 49. First arm 45 may be secured to distal end 27 of first port 16, second arm 47 may be secured to distal end 33 of second port 17, and third arm 49 may be secured to distal end 39 of third port 19. Sheath 21 may include a plurality of longitudinal lumens 51, 53 and 55, the proximal end of lumen 51 being aligned with lumen 29 of port 15, the proximal end of lumen 53 being aligned with lumen 35 of port 17, and the proximal end of lumen 55 being aligned with lumen 41 of port 19.

As will be discussed further below, sheath 21 is preferably appropriately dimensioned to permit its insertion into a desired anatomy, such as, in the present embodiment, to permit its transcervical insertion into a uterus. For such an application, sheath 21 is preferably about 22-25 cm in length.

In the illustrated embodiment, sheath 21 is provided with a dedicated fluid lumen 51, placing the proximal fluid port 16 in communication with a distal opening on fluid lumen 51. The dedicated fluid lumen 51 permits controllable and optimized fluid infusion rates, compared to a multi-function lumen such as in an alternate embodiment in which fluid is infused in the annular space surrounding another tool such as a visualization element or distension device. The dedicated fluid lumen 51 is preferable in an embodiment in which simultaneous tissue cutting and tissue removal is to be accomplished. Fluid may be introduced through the lumen 51 to the working site, to facilitate aspiration of morcellated or otherwise cut tissue through the tissue removal device and out of the patient. The dedicated fluid lumen 51 may be omitted, in an embodiment in which a grasper or other tool is repeatedly introduced and withdrawn through a working channel in order to remove the desired volume of tissue.

Visualization device 13, which may be used for direct visual observation of a uterus, may be, for example, a rod-lens hysteroscope or a flexible hysteroscope and is shaped to include a proximal end 63 and a distal end 65. Device 13 may be inserted into introducer 12 through third (visualization) port 19, preferably with proximal end 63 of device 13 not being inserted into introducer 12 and with distal end 65 of device 13 being positioned at or beyond distal end 43 of sheath 21.

In the illustrated embodiment, the visualization port 19 is in communication with a visualization lumen 55. Visualization lumen 55 extends throughout the length of the sheath 21 to the distal end. In one embodiment (not illustrated), the distal end of the visualization lumen 55 is provided with a transparent barrier such as a window or lens, so that the visualization lumen 55 has a closed distal end. This prevents the introduction of body fluids into the visualization lumen 55, and thereby avoids contamination of the visualization device 13. In this embodiment, the visualization device 13 may be advanced distally through visualization lumen 55 to a position at or about the location of the distal window, and visualization may be accomplished through the closed end of the visualization lumen 55 without contact between the hysteroscope and body fluids.

Distension device 14, which may be particularly well-suited for distending the uterus of a patient, comprises a mechanical expansion structure. Expansion of the expansion structure can be accomplished either actively or passively, depending upon the desired clinical functionality. Active expansion occurs in response to the application of force by the clinician, which may be accomplished in of a variety of ways. For example, rotatable knobs, slider switches, thumb wheels or other controls may be actuated to axially proximally retract or distally advance an actuation wire, or rotate a threaded shaft. An electrical signal can be utilized to activate an electromechanical expansion structure, or any of a variety of inflation media including gas or liquid can be utilized to activate an inflatable component on an active expansion structure. Passive expansion structures include structures which will self expand following the removal of a restraint. When in a constrained configuration, the passive mechanical expansion structures typically exhibit a spring force bias in the direction of the expanded configuration. This may be accomplished using any of a variety of spring constructions, and also through the use of shape memory materials such as various Nitinol or elgiloy alloys, in some instances stainless steel, and shape memory polymeric material which are known in the art.

In the present embodiment, said mechanical expansion structure comprises a self-expanding scaffolding 83. Scaffolding 83 may include a resiliently-biased foldable weave of filaments 84 made of Nitinol (nickel-titanium alloy) shape-memory alloy, spring steel or a similar shape-memory material. Scaffolding 83 may be constructed so that, when fully expanded within a uterus, it distends the uterus or a portion of the uterus to a desired extent. If desired, scaffolding 83 may be constructed so that its expanded shape mimics the shape of the uterus. Preferably, scaffolding 83 is constructed to distend the uterus to an extent equivalent to that which would be attained using the above-described conventional fluid distension technique at a pressure of at least 40 mm Hg but not greater than 100 mm Hg and preferably at a pressure of approximately 70 mm Hg. If desired, scaffolding 83 may be constructed to provide a uniform radial force in all directions or may be constructed to provide different radial forces in different directions, such as along the coronal and sagittal planes.

The woven filaments 84 making up scaffolding 83 may be sized and spaced (e.g., diameter, length, width) to effectively cover a small portion of the contacted surface area, thereby leaving one or two or more large working "windows" between adjacent filaments 84 through which diagnostic and/or therapeutic tool may be advanced and/or procedures may be performed, or the members may be sized and spaced to cover a large portion of the contacted surface area, with comparatively smaller "windows." It should be noted that, by appropriately sizing and positioning such "windows" over a target tissue, scaffolding 83 may cause a target tissue to avulse through a window and into the interior of scaffolding 83, where it may then be treated. (As seen in FIGS. 3(d) and 4(c), scaffolding 83 may additionally be provided with an enlarged window 86, which may be used to provide facile access to target tissue from within scaffolding 83.)

Distension device 14 may further comprise an outer sheath 85. Sheath 85, which may be a unitary, tubular member, has a proximal end 87 and a distal end 89. Sheath 85 may be inserted into introducer 12 through second port 17, preferably with proximal end 87 remaining external to introducer 12 and with distal end 89 being positioned at or beyond distal end 43 of sheath 21. As will be discussed further below, when scaffolding 83 is positioned within sheath 85, scaffolding 83 is maintained in a compressed state by sheath 85. By contrast, when scaffolding 83 is positioned distally relative to sheath 85, scaffolding 83 may self-expand.

Distension device 14 may further comprise a tie-line 91 and an ejector rod 92. Tie-line 91 may have a proximal end 93 extending proximally from sheath 85 and a distal end fixed to scaffolding 83. Ejector rod 92 may be slidably and removably mounted within sheath 85 for ejecting scaffolding 83 distally from sheath 85.

Tissue modifying device 15 may comprise a morcellator and/or another tissue modifying device including, for example, a drug delivery device. In the present embodiment, tissue modifying device 15 is a morcellator, which may be used to remove abnormalities, such as fibroids and polyps, from a uterus. The morcellator may be conventional in size, shape and construction, and may have a proximal end 97 and a distal end 99. Tissue modifying device 15 may be inserted into introducer 12 through second port 17, preferably with proximal end 97 not being inserted into introducer 12 and with distal end 99 being positioned at or beyond distal end 43 of sheath 21.

Figure 3B:
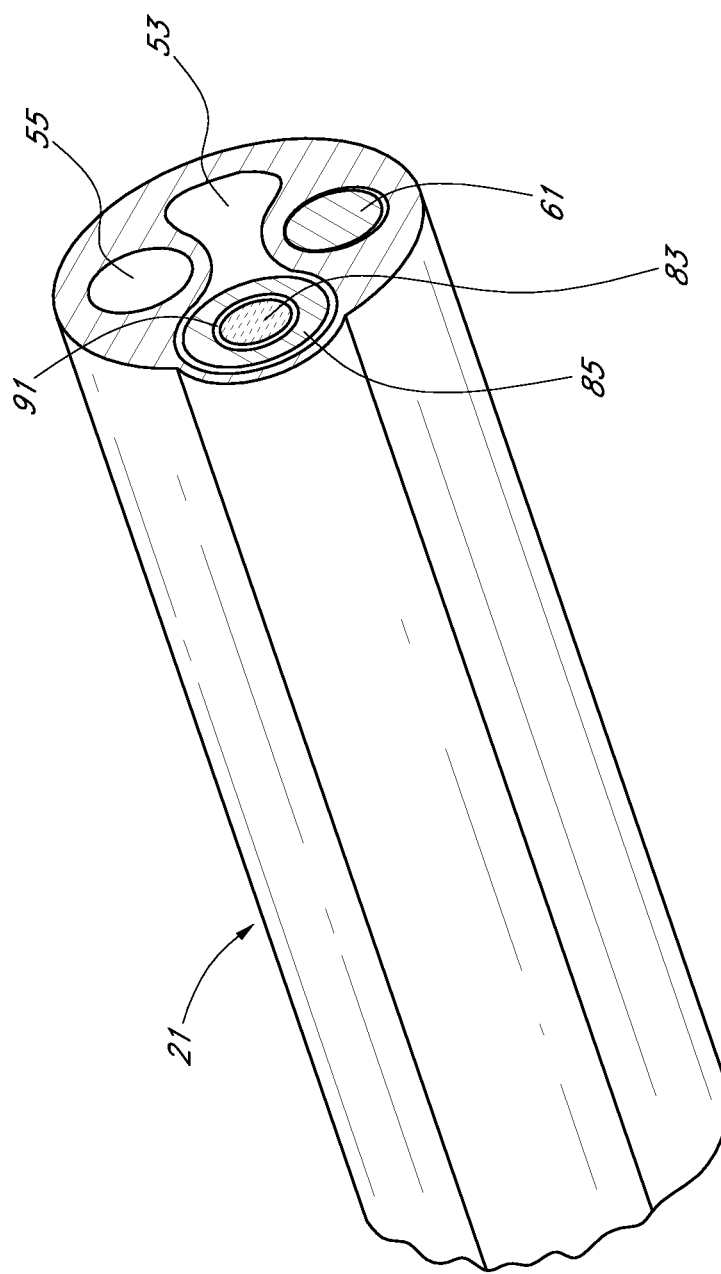
Figure 3C:
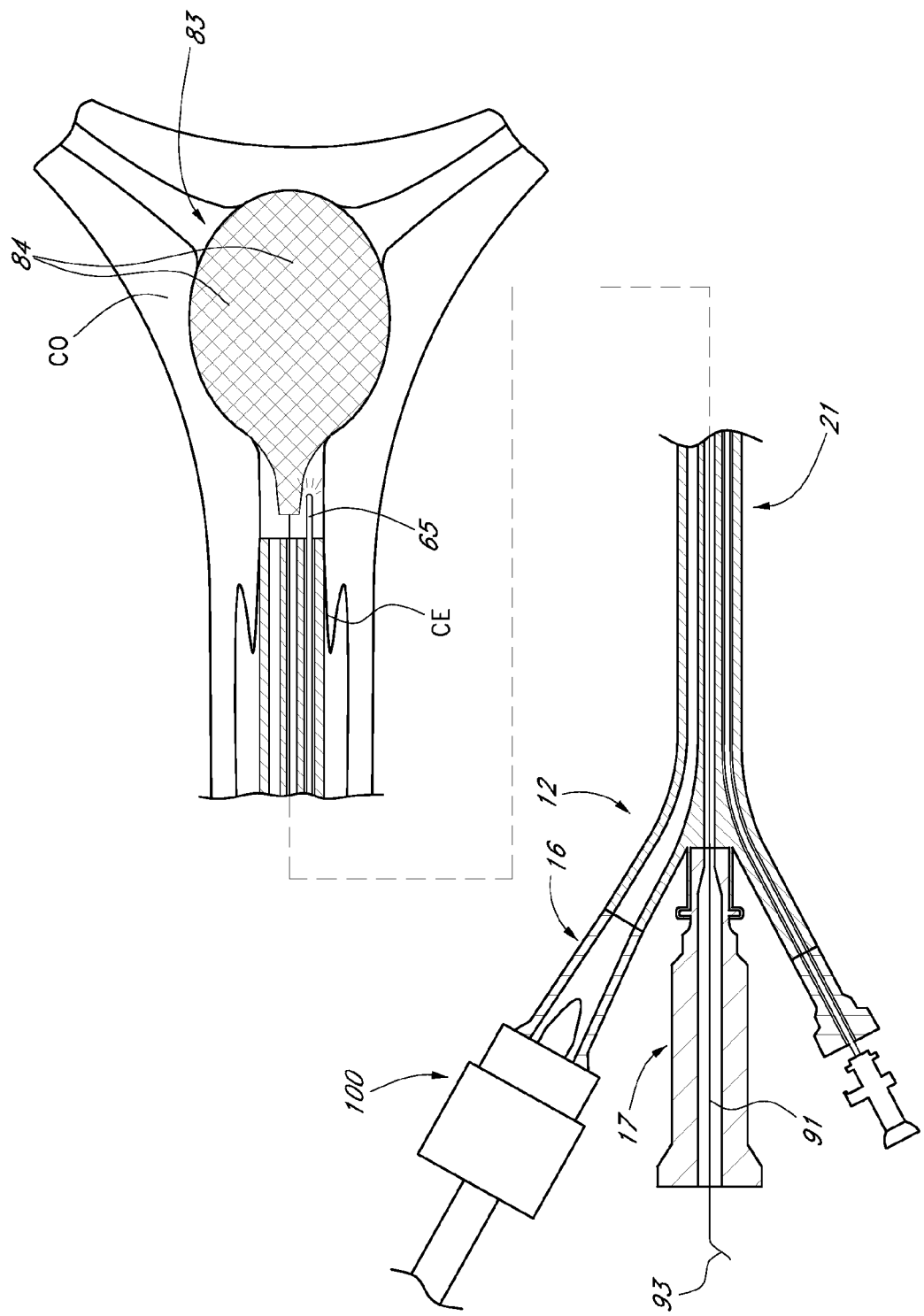
Figure 3D:
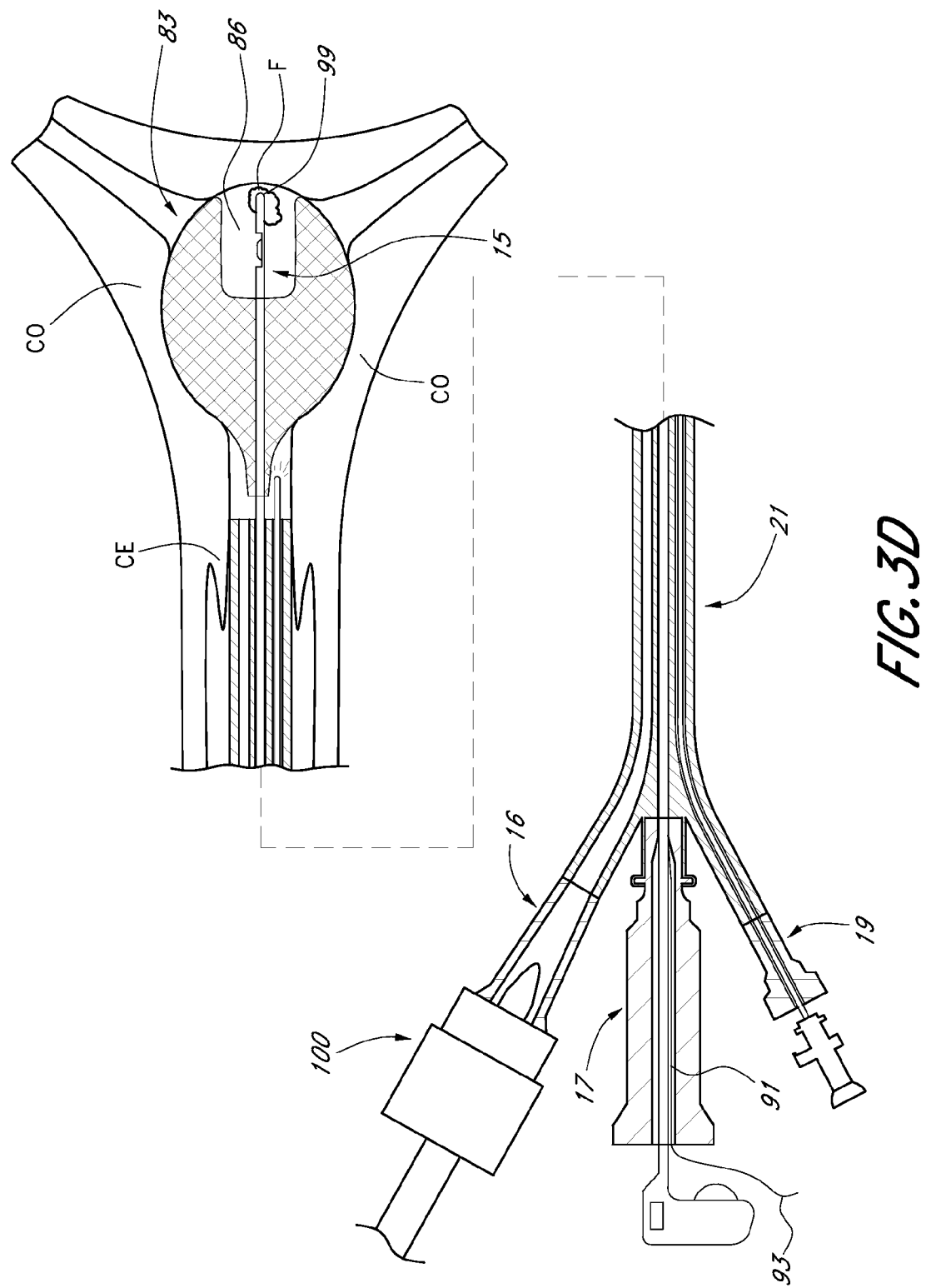

Referring now to FIGS. 3(a) through 3(f), there is shown one way in which system 11 may be used to perform a medical procedure. For illustrative purposes, system 11 is shown in FIGS. 3(a) through 3(f) being used to remove a fibroid F from a uterus; however, it should be understood that system 11 may be used to perform other types of medical procedures, whether in the uterus or otherwise. First, as seen in FIG. 3(a), with visualization device 13 loaded into introducer 12 through third port 19, and with a fluid source, such as a fluid-containing syringe 100, coupled to first port 16, distal end 43 of sheath 21 is inserted transcervically into the patient up to the os (i.e., the portion of the anatomy where the cervix CE transitions to the corpus CO). At this time, it may be desirable to dispense at least some of the fluid contained in syringe 100 through lumen 51 to wash distal end 65 of visualization device 13 (as mucus, blood and other debris may have become deposited on distal end 65 of visualization device 13 during the insertion of visualization device 13 into the patient), unless a closed visualization lumen is used as discussed above, as well as to flush the uterus. Next, distension device 14 is loaded into introducer 12 through second port 17 so that distal end 89 of sheath 85 is positioned at or beyond distal end 43 of sheath 21. As seen in transverse cross-section in FIG. 3(b), the insertion of distension device 14 into sheath 21 causes sheath 21 to expand radially to accommodate distension device 14. To minimize discomfort to the patient, such as by obviating the need for administration of anesthetic to the patient, the expanded cross-sectional diameter of sheath 21 is preferably less than about 5.5 mm, more preferably less than about 5.0 mm.

Next, ejector rod 92 is used to eject scaffolding 83 distally from sheath 85, whereby scaffolding 83 automatically self-expands to distend corpus CO. Ejector rod 92 and sheath 85 are then removed proximally from introducer 12. As seen in FIG. 3(c), this leaves scaffolding 83 deployed in the uterus, with the distal end of tie-line 91 connected to scaffolding 83 and proximal end 93 of tie-line 91 passing through introducer 12 and remaining external to the patient. It may be noted that the removal of ejector rod 92 and sheath 85 from introducer 12 causes sheath 21 to return back to its original transverse cross-sectional size. With the uterus thus distended by scaffolding 83, a visual examination of the uterus may be conducted using visualization device 13. In the event that a fibroid or other abnormality is detected that one wishes to remove, then, as seen in FIG. 3(d), tissue modifying device 15 is loaded into introducer 12 through second port 17 along side of tie-line 91, tissue modifying device 15 being moved distally until positioned in the area of the fibroid F one wishes to remove. (Scaffolding 83 is shown in FIG. 3(d) with an enlarged window 86 to provide facile access to target tissue through scaffolding 83.) As seen in transverse cross-section in FIG. 3(e), the insertion of tissue modifying device 15 into sheath 21 again causes sheath 21 to expand radially. Once again, to minimize discomfort to the patient, such as by obviating the need for administration of an aesthetic to the patient, the expanded cross-sectional diameter of sheath 21 is preferably less than about 5.5 mm, more preferably less than about 5.0 mm.

With tissue modifying device 15 thus introduced into the patient, device 15 is used to remove fibroid F. When tissue modifying device 15 is no longer needed, device 15 is withdrawn proximally from introducer 12. The withdrawal of tissue modifying device 15 from introducer 12 causes sheath 21 to return back to its original transverse cross-sectional size. Sheath 85 is then inserted over tie-line 91 and loaded back into introducer 12, causing sheath 21 again to expand radially. Then, as seen in FIG. 3(f), tie-line 91 is pulled proximally until scaffolding 83 is drawn back into sheath 85. The retraction of scaffolding 83 into sheath 85, in turn, causes corpus CO to return to its relaxed state. Finally, the components of system 11 that still remain in the patient are removed proximally from the patient.

As compared to existing systems for accessing, examining and/or treating fibroids in a uterus, system 11 possesses the benefit of not requiring that a fluid be used to distend the uterus. Instead, as illustrated above, system 11 uses mechanical means to distend the uterus. Fluid may be used, however, for irrigation and aspiration purposes, and to clear the optical field. This may be accomplished by introduction of fluid through fluid lumen 51, and aspiration through working lumen 53.

Figure 4A:
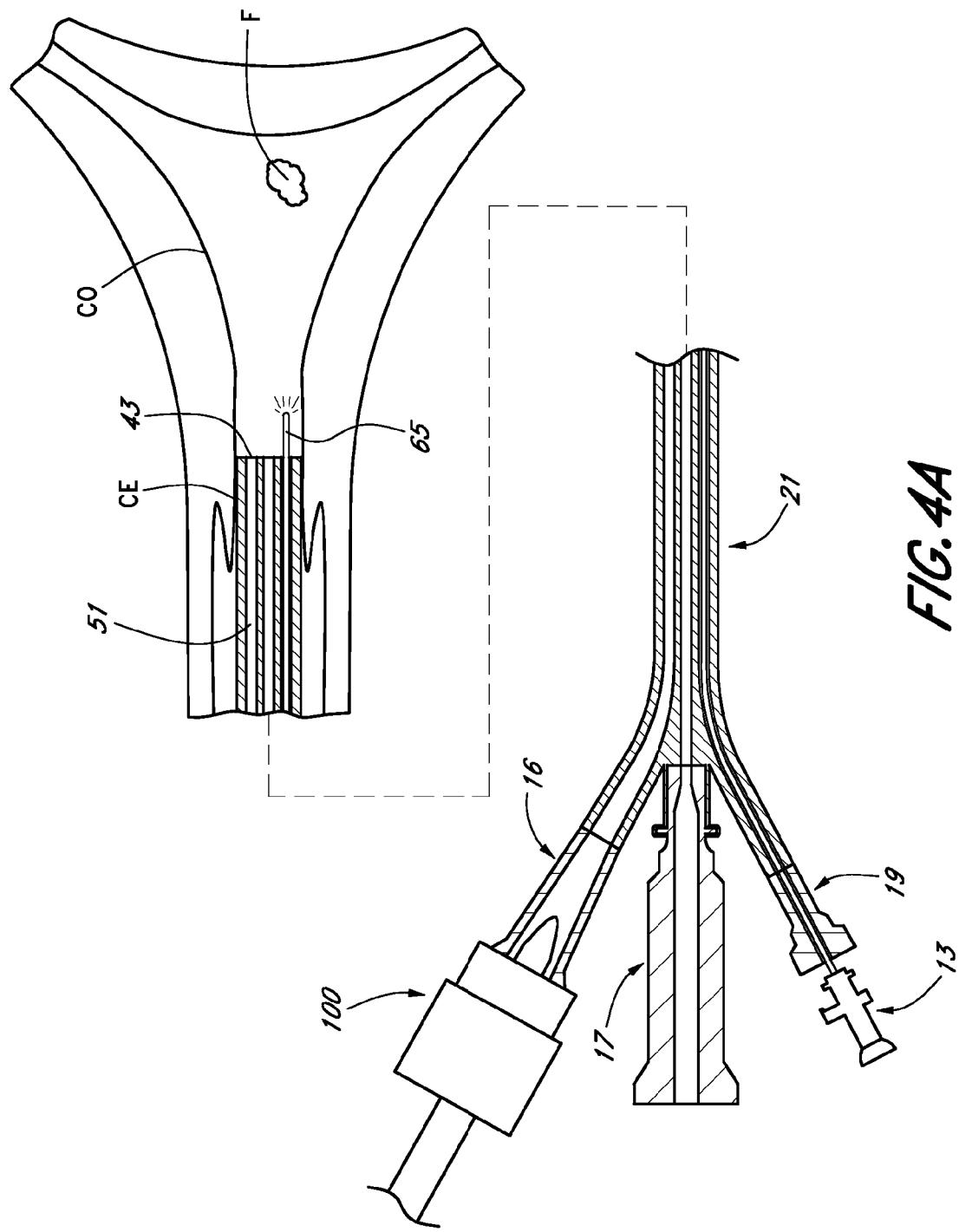
Figure 4B:
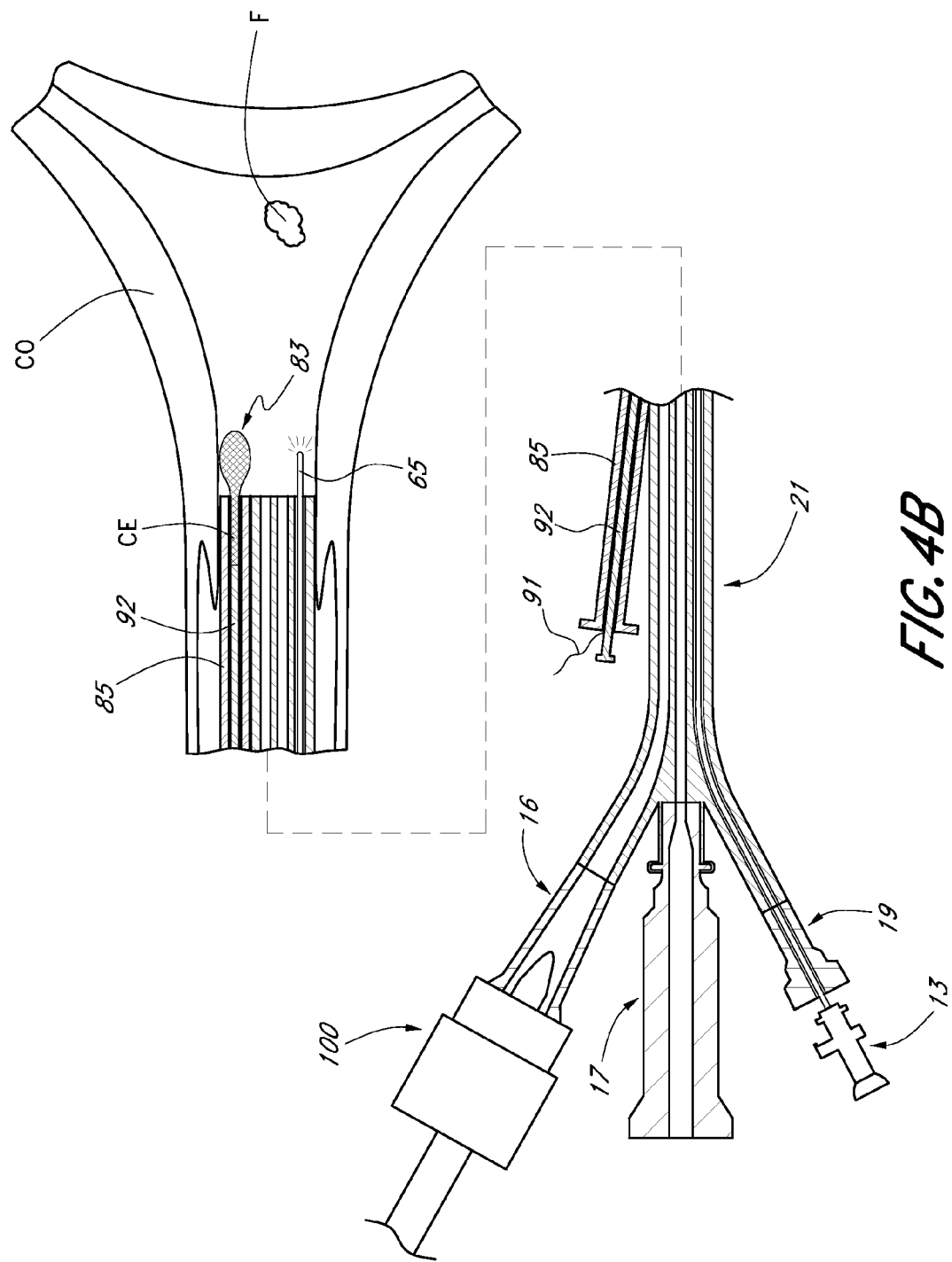
Figure 4C:
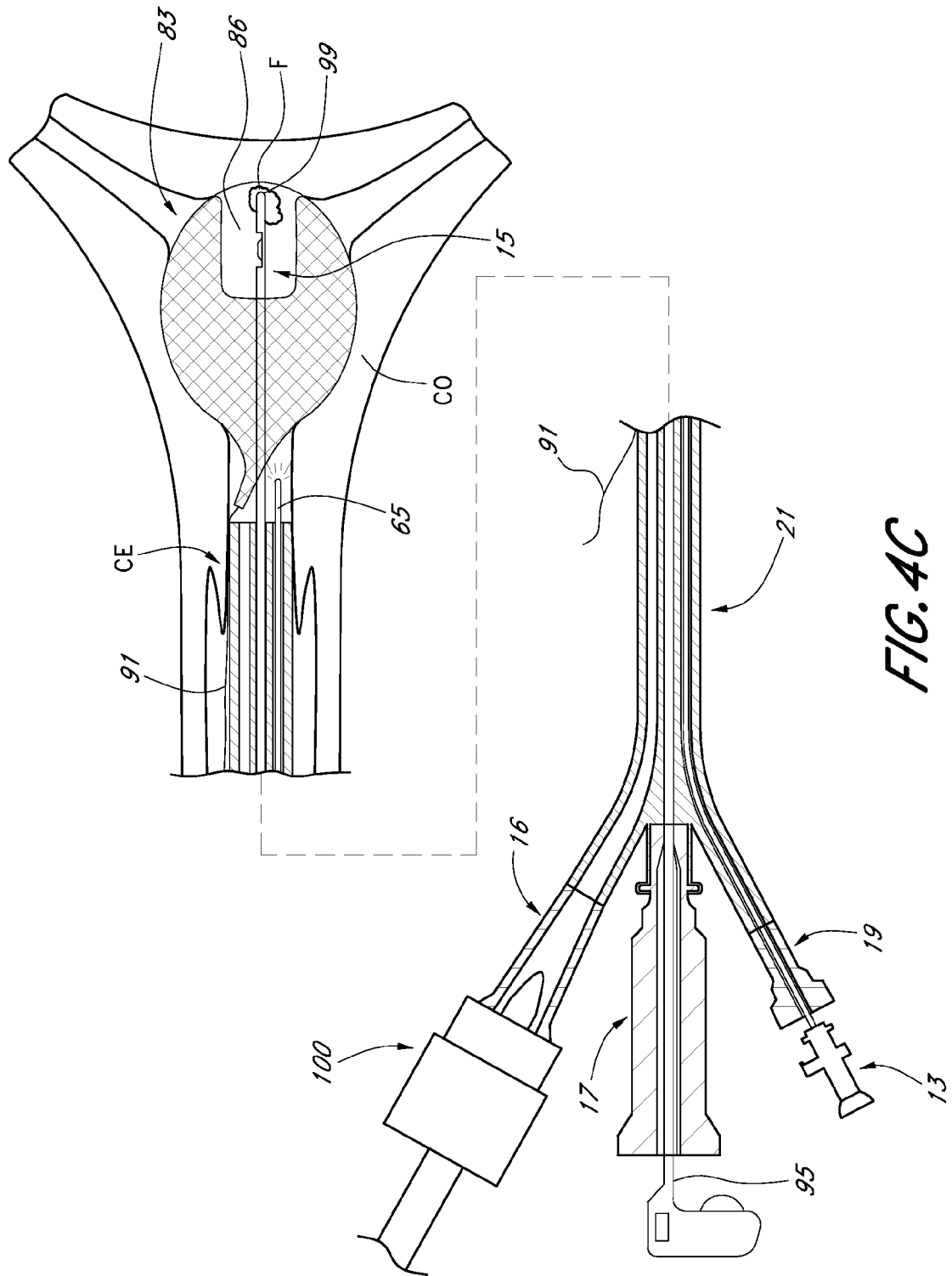

Referring now to FIGS. 4(a) through 4(d), there is shown another way in which system 11 may be used to perform a medical procedure. For illustrative purposes, system 11 is shown in FIGS. 4(a) through 4(d) being used to remove a fibroid from a uterus; however, it should be understood that system 11 may be used to perform other types of medical procedures, whether in the uterus or otherwise. First, as seen in FIG. 4(a), with visualization device 13 loaded into introducer 12 through third port 19, and with a fluid source, such as a fluid-containing syringe 100, coupled to first port 16, distal end 43 of sheath 21 is inserted transcervically into the patient up to the os. At this time, it may be desirable to dispense at least some of the fluid contained in syringe 100 through lumen 51 to wash distal end 65 of visualization device 13, as well as to flush the uterus.

Next, distension device 14 is inserted transcervically into the patient up to the os. However, it should be noted that, as compared to the technique discussed above in which distension device 14 is inserted through introducer 12, distension device 14 is inserted in the present embodiment parallel to, but outside of, introducer 12. To minimize discomfort to the patient, such as by obviating the need for administration of an aesthetic to the patient, the combined cross-sectional diameter of sheath 21 and distension device 14 is preferably less than about 5.5 mm, more preferably less than about 5.0 mm.

Next, as seen in FIG. 4(b), ejector rod 92 is used to eject scaffolding 83 distally from sheath 85, whereby scaffolding 83 automatically self-expands to distend corpus CO. Ejector rod 92 and sheath 85 are then removed proximally from the patient, leaving scaffolding 83 deployed in the uterus, with proximal end 93 of tie-line 91 remaining external to the patient. With the uterus thus distended by scaffolding 83, a visual examination of the uterus may be conducted using visualization device 13. In the event that a fibroid F or other abnormality is detected that one wishes to remove, then, as seen in FIG. 4(c), tissue modifying device 15 is loaded into introducer 12 through second port 17 and is inserted into the distended uterus. (Scaffolding 83 is shown in FIG. 4(c) with an enlarged window 86 to provide facile access to target tissue through scaffolding 83.) The insertion of the tissue modifying device 15 into sheath 21 causes sheath 21 to expand radially. To minimize discomfort to the patient, such as by obviating the need for administration of an aesthetic to the patient, the combined cross-sectional diameter of sheath 21 and tie-line 91 is preferably less than about 5.5 mm, more preferably less than about 5.0 mm.

With tissue modifying device 15 thus introduced into the uterus of the patient, device 15 may then be used to remove fibroid F. When tissue modifying device 15 is no longer needed, device 15, introducer 12 and visualization device 13 are withdrawn proximally from the patient. Sheath 85 is then inserted distally over proximal end 93 of tie-line 91 and is re-introduced transcervically into the patient. Then, as seen in FIG. 4(d), tie-line 91 is then pulled proximally until scaffolding 83 is retracted into sheath 85. The retraction of scaffolding 83 into sheath 85, in turn, causes corpus CO to return to its relaxed state. Scaffolding 83 and sheath 85 are then removed proximally from the patient.

According to yet another embodiment (not shown), prior to inserting introducer 12 and visualization device 13 into the patient, distension device 14 is inserted transcervically into the patient, scaffolding 83 is deployed in the uterus, and ejector rod 92 and sheath 85 are removed from the patient. Introducer 12 and visualization device 13 are then inserted into the patient, with introducer 12 being inserted along side of tie-line 91. The uterus may then be examined and treated in the manner described above. Alternatively, prior to inserting distension device 14 into the patient, one could insert introducer 12 and visualization device 13 into the patient, use visualization device 13 to take a quick look at the uterus to make sure that there is no reason why distension device 14 should not be used, remove introducer 12 and visualization device 13 from the patient and then, assuming no reason was detected to preclude using distension device 14, proceed in the fashion described above.

Figure 5:
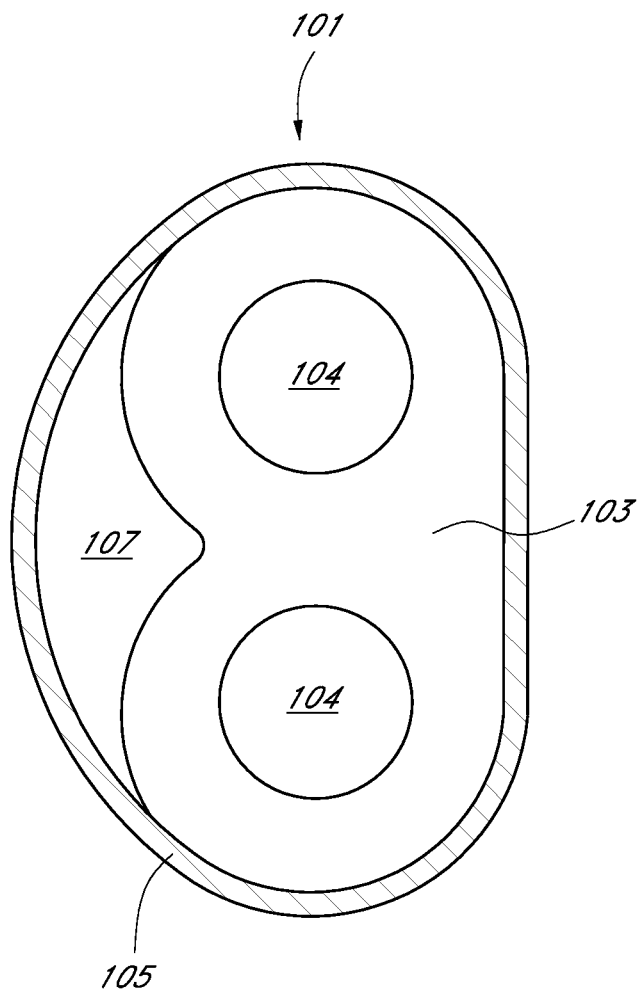
FIG. 5 is a section view of an alternate sheath to the sheath shown in FIG. 1.
Figure 6:
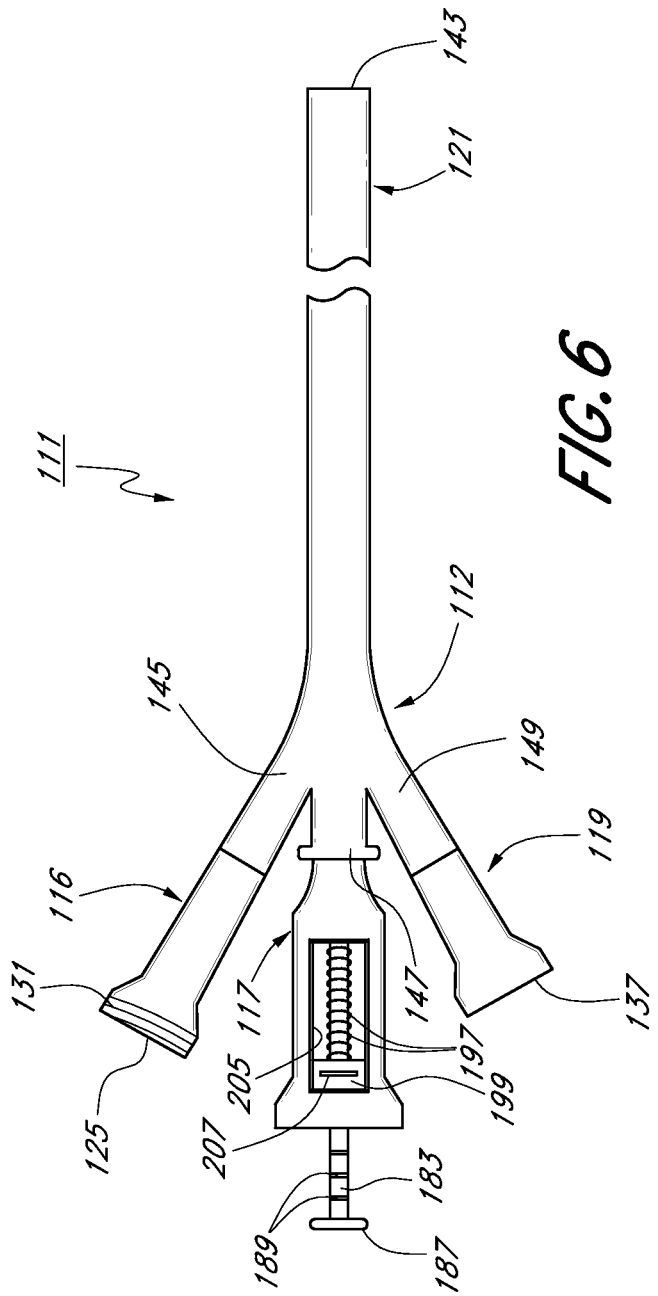
FIG. 6 is a plan view of a second embodiment of a system for use in accessing and in examining and/or treating a body cavity, the system being constructed according to the teachings of the present invention, with the mechanical expansion structure shown in a retracted and non-expanded state.

Referring now to FIG. 5, there is shown a section view of an alternate sheath which may be used instead of sheath 21 as part of introducer 12, the alternate sheath being constructed according to the teachings of the present invention and represented generally by reference numeral 101.

Sheath 101, which preferably is flexible, may comprise an inner member 103 and an outer film 105. Inner member 103, which may be made of a semi-rigid material, is shaped such as by extrusion to include a first lumen 104 and a second lumen 106. First lumen 104 may be aligned with longitudinal lumen 29 of first port 16, and second lumen 106 may be aligned with longitudinal lumen 41 of port 19.

Outer film 105 and inner member 103 jointly define a third lumen 107, which may be aligned with longitudinal lumen 35 of port 17. Preferably, film 105 is an elastic material capable of radial expansion so that third lumen 107 may expand when distension device 14 or tissue modifying device 15 is inserted into lumen 107 and may return to a compact state when neither is inserted into lumen 107.

Referring now to FIGS. 6 through 10, there are shown various views of a second embodiment of a system for use in accessing and in examining and/or treating a body cavity, the system being constructed according to the teachings of the present invention and being represented generally by reference numeral 111.

System 111, like system 11, is particularly well-suited for use in accessing and in examining and/or treating the uterus of a female patient. However, it should be understood that system 111 is not limited to such a use and may be used in other anatomies that may be apparent to those of ordinary skill in the art.

System 111 may comprise an introducer 112, a visualization device 113, a distension device 114 and a tissue modifying device 115. Introducer 112, in turn, may include a first member 116, a second member 117, a third member 119, and a sheath 121. Members 116, 117 and 119 are typically not intended for insertion into a patient whereas the distal end of sheath 121 is typically intended for insertion into a patient. First member 116, which may be adapted to receive, for example, the distal end of a fluid-containing syringe (not shown) or another fluid source, may be shaped to include a proximal end 125, a distal end (not shown) and a longitudinal lumen (not shown). A helical thread or luer lock 131 may be provided on the exterior of member 116 near proximal end 125 to matingly engage a complementary thread or luer lock on a syringe or the like. Second member 117, which may be adapted to receive, for example, distension device 114 and tissue modifying device 115, may be shaped to include a proximal end 131, a distal end (not shown) and a pair of longitudinal lumens 135 and 136. Third member 119, which may be adapted to receive, for example, visualization device 113, may be shaped to include a proximal end 137, a distal end (not shown) and a longitudinal lumen (not shown). Each of first member 116, second member 117, and third member 119 may be made of a rigid material, such as a rigid, medical grade plastic.

Sheath 121 may be an elongated member made of an elastic material capable of radial expansion in one or more places. Sheath 121 may be shaped to include a branched proximal end and an unbranched distal end 143. The branched proximal end of sheath 121 may include a first arm 145, a second arm 147 and a third arm 149. First arm 145 may be secured to the distal end of first member 116, second arm 147 may be secured to the distal end of second member 117, and third arm 149 may be secured to the distal end of third member 119. Sheath 121 may include a plurality of longitudinal lumens 151, 153, 154 and 155, the proximal end of lumen 151 being located in first arm 145 and aligned with the lumen of member 116, the proximal end of lumen 153 being located in second arm 147 and aligned with lumen 135 of member 117, the proximal end of lumen 154 being located in second arm 147 and aligned with lumen 136 of member 117, and the proximal end of lumen 155 being located in third arm 149 and aligned with the lumen of member 119.

Sheath 121 is preferably appropriately dimensioned to permit its insertion into a desired anatomy, such as, in the present embodiment, to permit its transcervical insertion into a uterus.

Visualization device 113, which may be used for direct visual observation of a uterus, may be, for example, a rod-lens hysteroscope or a flexible hysteroscope. (For simplicity and clarity, visualization device 113 is shown only in FIG. 10 and is showed therein in simplified form.) Device 113 may be inserted into introducer 112 through third member 119, preferably with the proximal end of device 113 not being inserted into introducer 112 and with the distal end of device 113 being positioned at or beyond distal end 143 of sheath 121.

Distension mechanism 114, which may be particularly well-suited for distending the uterus of a patient, may comprise an elongated structure slidably disposed in lumens 135 and 153. The elongated structure may comprise a proximal portion 183 and a distal portion 185. Proximal portion 183 may be an elongated member having a handle 187 at its proximal end and a plurality of teeth 189 along its top surface. Proximal portion 183 may be made of a rigid material, such as a rigid, medical grade plastic. Distal portion 185 may be an elongated member preferably made of a resilient material, such as Nitinol (nickel-titanium alloy) shape-memory alloy, spring steel, a shape-memory plastic, or a similar shape-memory material.

Distal portion 185 may be bent at a point 188, with one end 191 of distal portion 185 being fixed to the distal end 190 of proximal portion 183 and the opposite end 193 of distal portion 185 being fixed to a ring 195 slidably inserted over an intermediate portion of distal portion 185. As a result, as can be seen by comparing FIGS. 7 and 8, when ring 195 is distally advanced to a position proximate to point 188 (FIG. 8), distal portion 185 "bows out" to assume an expanded shape. Alternatively, when ring 195 is proximally retracted with respect to point 188, distal portion 185 assumes a non-expanded shape.

As can be appreciated, distal portion 185 may be constructed so that, when fully expanded within a uterus, it distends the uterus or a portion of the uterus to a desired extent. If desired, distal portion 185 may be constructed so that its expanded shape mimics the shape of the uterus. Preferably, distal portion 185 is constructed to distend the uterus to an extent equivalent to that which would be attained using the above-described conventional fluid distension technique at a pressure of at least 40 mm Hg but not greater than 100 mm Hg and preferably at a pressure of approximately 70 mm Hg.

Distension mechanism 114 may additionally include a mechanism for selectively positioning ring 195 so that distal portion 185 may assume an expanded shape at any desired point within a working range in between a fully expanded shape and a non-expanded shape. Said ring-positioning mechanism may comprise a biasing mechanism such as coiled spring 197 and a control such as switch 199. Coiled spring 197, which may be inserted coaxially over adjacent sections of proximal portion 183 and distal portion 185, may have a proximal end 201 fixed to switch 199 and a distal end 203 fixed to ring 195. Switch 199, which may be inserted coaxially over proximal portion 183, is accessible through a transverse slot 205 in second member 117 and is adapted for sliding movement back and forth between the proximal and distal ends of slot 205. A pawl 207 may be pivotally mounted in switch 199 to engage teeth 189 in a ratchet-like fashion. In this manner, when switch 199 is moved distally within slot 205, undesired proximal movement of switch 199 is prevented. However, when one wishes to return switch 199 to its proximal position, pawl 207 may be pivoted away from engagement with teeth 189, thereby allowing spring 197 to decompress, which, in turn, causes switch 199 to be moved back to its proximal position.

Tissue modifying device 115 may comprise a morcellator or other mechanical cutting tool, or a transducer or emitter for any of a variety of energy forms such as laser, ultrasound, RF or others known in the art. Another tissue treating device includes, for example, a drug delivery device. In the present embodiment, tissue modifying device 115 is a side opening or end opening morcellator, which may be used to remove abnormalities, such as fibroids and polyps, from a uterus. (For simplicity and clarity, tissue modifying device 115 is shown only in FIG. 10 and is shown therein in simplified form.) Tissue modifying device 115 may be inserted into introducer 112 through lumen 136 of second member 117, preferably with the proximal end of device 115 not being inserted into introducer 112 and with the distal end of device 115 being positioned at or beyond distal end 143 of sheath 121.

One way in which system 111 may be used is as follows: First, system 111 is prepped by loading visualization device 113 into introducer 112 through third member 119 and by ensuring that distension mechanism 114 is in its retracted and non-expanded state (as in FIGS. 6 and 9). In addition, a fluid source, such as a fluid-containing syringe, is preferably coupled to first member 116. Next, distal end 143 of sheath 121 is inserted transcervically into the patient up to the os. At this time, it may be desirable to dispense at least some of the fluid contained in the syringe through lumen 151 to wash the distal end of visualization device 113, as well as to flush the uterus. Next, distension mechanism 114 is placed in its advanced and non-expanded state (as in FIG. 7) by moving proximal portion 183 distally until handle 187 abuts proximal end 131 of second member 117. (Pawl 207 will need to be pivoted out of engagement with teeth 189 as proximal portion 183 is moved distally.) Next, distension mechanism 114 is placed in its advanced and expanded state (as in FIG. 8) by moving switch 199 from its proximal position within slot 205 to its distal position within slot 205. With the uterus thus distended, a visual examination of the uterus may be conducted using visualization device 113. In the event that a fibroid or other abnormality is detected that one wishes to remove, then the tissue modifying device 115 is loaded into introducer 112 through lumen 136 of second member 117 and into lumen 154 of sheath 121. As seen in FIG. 10, the introduction of tissue modifying device 115 into lumen 154 causes sheath 121 to be distended. Next, tissue modifying device 115 is moved distally until positioned in the area of the fibroid or other abnormality one wishes to remove. Tissue modifying device 115 is then used to remove the fibroid. When tissue modifying device 115 is no longer needed, device 115 is withdrawn proximally from introducer 112. Distension mechanism 114 is then placed in its advanced and non-expanded state by moving pawl 207 out of engagement with teeth 189, thereby causing spring 197 to pull ring 195 away from point 188 (and causing switch 199 to be moved back to the proximal end of slot 205). Distension mechanism 114 is then placed in its retracted and non-expanded state by pulling handle 187 proximally until distal portion 185 is retracted into sheath 121. Finally, the components of system 111 that still remain in the patient are removed proximally from the patient.

In the various embodiments discussed above, although fluid may be used to flush the uterus and/or the distal end of the visualization device, non-fluid mechanical means are used to distend the uterus. However, according to a further aspect of the invention, fluid means are used initially to distend the uterus, and non-fluid mechanical means are thereafter used to maintain the uterus in its distended state. As can be appreciated, this two-part distension technique is not limited to the particular types of distension devices described above.

Referring now to FIG. 11, there is shown a plan view of a mechanical expansion device suitable for use in practicing the aforementioned two-part distension method, the mechanical expansion device being constructed according to the teachings of the present invention and being represented generally by reference numeral 301.

Device 301 may comprise a pair of arms 303 and 305. A pressure pad 307 may be mounted on the outer end of arm 303, and a pressure pad 308 may be mounted on the outer end of arm 305. The inner ends of arms 303 and 305 may be joined to a spring 309 that biases arms 303 and 305 away from one another. A loop 311, whose purpose will become apparent below, may be positioned adjacent to spring 309.

Referring now to FIGS. 12(a) and 12(b), there is shown one way in which device 301 may be used to maintain a uterus in a distended state. In FIG. 12(a), a pair of devices 301 are shown loaded into lumen 53 of introducer 13, introducer device 13 having been inserted transcervically into a patient up to the os. The uterus of the patient is shown distended with a distension fluid, which preferably has previously been delivered to the uterus by means of a fluid-containing syringe (not shown) coupled to lumen 51. Devices 301 may be ejected from lumen 53 of introducer device 13 into the distended uterus by an ejector rod 315. In FIG. 12(b), devices 301 are shown deployed in the uterus to maintain the uterus in its already distended state. With the uterus thus maintained in its distended state, a morcellator or other desired tool may be inserted through lumen 53 of introducer 13 into the uterus. When distension of the uterus is no longer desired, devices 301 may be removed from the uterus by inserting a hook 319 or similar structure into the uterus through introducer 13, using hook 319 to grasp devices 301 by their respective loops 311, and then pulling hook 319 proximally to retract the hooked devices 301 into lumen 53 of introducer 13.

In general, the mechanical distension device is thus any of a wide variety of structures which are capable of translumenal introduction through the working channel in a first, reduced cross sectional profile and transformation to a second, enlarged cross sectional profile once in the vicinity of the treatment site. The second, enlarged cross sectional profile creates a sufficient space at the site to allow manipulation of diagnostic or therapeutic tools necessary for the intended procedure. This may be, for example, equivalent to at least the volume of the cavity created by 70 to 80 mm Hg of fluid distension.

Typically, the distension provided by a fluid or gas is diffuse in nature. Rather than creating a discrete working space at the desired treatment site, the media expands the associated cavity without preference. In the case of uterine distension, a fluid pressure of 35 to 60 mm Hg typically produces a cavity of 10 to 50 cc in total volume. But the volume of the distension media is distributed evenly throughout the entire uterus, so that the effective working space provided in the immediate vicinity of any particular treatment site is relatively small compared to the total volume of the cavity. The addition of additional pressure that can reach 100 to 120 mm Hg does provide additional cavity volume but at the risk of fluid intravasation and greater pain for the patient.

One particular advantage of the mechanical distension structures in accordance with the present invention is the ability to create a specific working space at a desired site, while leaving other parts of the cavity in its collapsed configuration. By localizing the distension to the desired site, the size of the working cavity at that site can be optimized while minimizing the total volume of the distension and the associated pain for the patient.

For example, it may be desirable to provide a working space in the immediate vicinity of a treatment site having dimensions that would approximate a 10 cc sphere. To create that same working space by infusion of distension media, the infused volume may need to be at least about 40 cc or 50 cc or more. Thus, in accordance with the present invention, the working space created at the desired site is at least about 50%, often at least about 70% and preferably at least about 85% of the enclosed volume of the expandable portion of the distension device. The working space may be approximately equal to the volume of the expanded device, which may be less than about 50%, often less than about 35% and preferably less than about 25% of the volume of distension media which would be necessary to achieve a similar working volume at the treatment site.

The expansion device may be permanently attached to the distal end of an operating shaft, permanently attached to the distal end of a tether, or detachable at the treatment site. Any of a wide variety of detachable expansion structures may be subsequently removed by advancing a grasper down the working channel and grasping the device under endoscopic visualization. The device may be thereafter be proximally retracted into the working channel and reduced in cross section for removal.

In general, the tissue distension structure will have at least a first surface for contacting a first tissue zone and a second surface for contacting a second tissue zone. Activation of the distension structure advances the first and second surfaces away from each other, to enlarge the distance between the first and second tissue zones. In the embodiment illustrated in FIGS. 7 and 8, for example, the tissue distension structure opens such that it resides substantially within a single plane which contains the longitudinal axis of the device. In alternative embodiments, the tissue distension structure may open in two transverse planes having an intersection along the longitudinal axis of the device, or such that the distension structure opens into a more complex three dimensional configuration, including spherical, elliptical, and other geometric forms of rotation about an axis. In each instance, the tissue distension device preferably includes at least one opening in a side or end wall thereof, to permit access to the target tissue.

Figure 7:
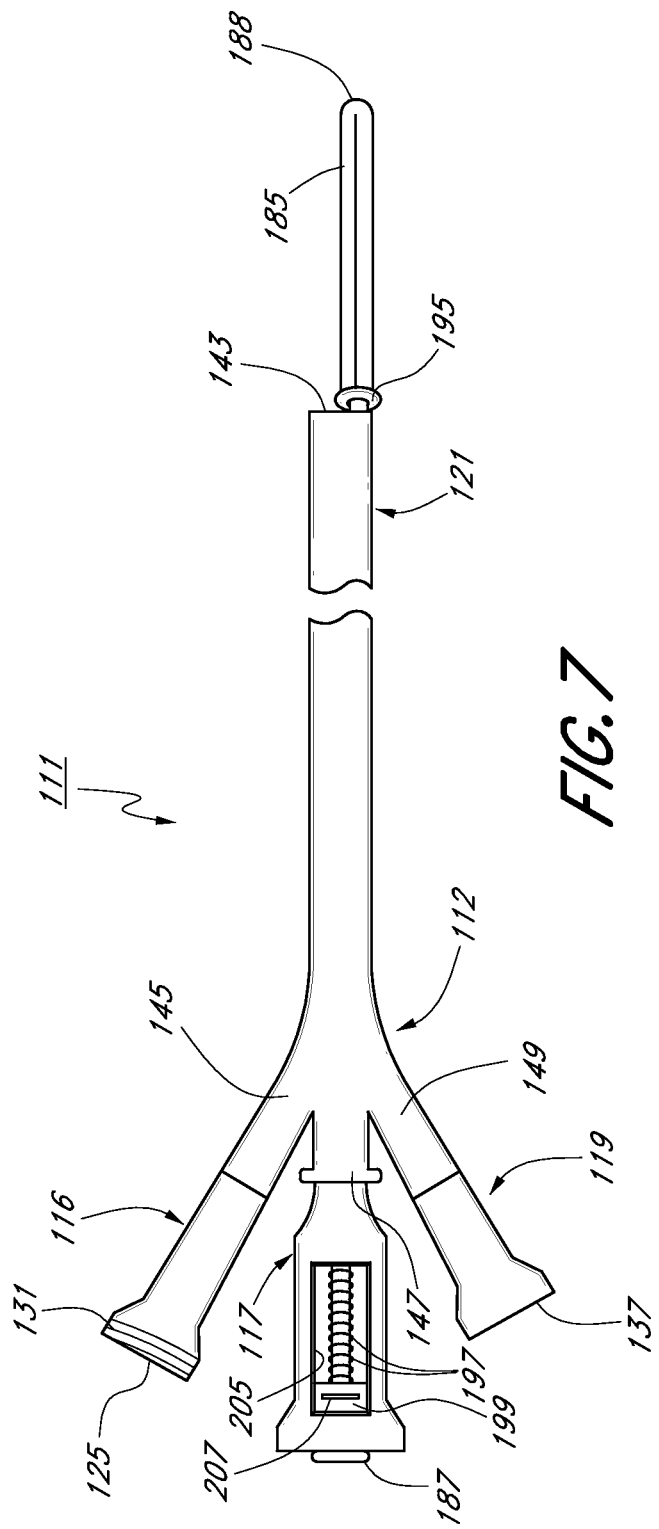
FIG. 7 is a plan view of the system shown in FIG. 6, with the mechanical expansion structure shown in an advanced and non-expanded state.
Figure 8:
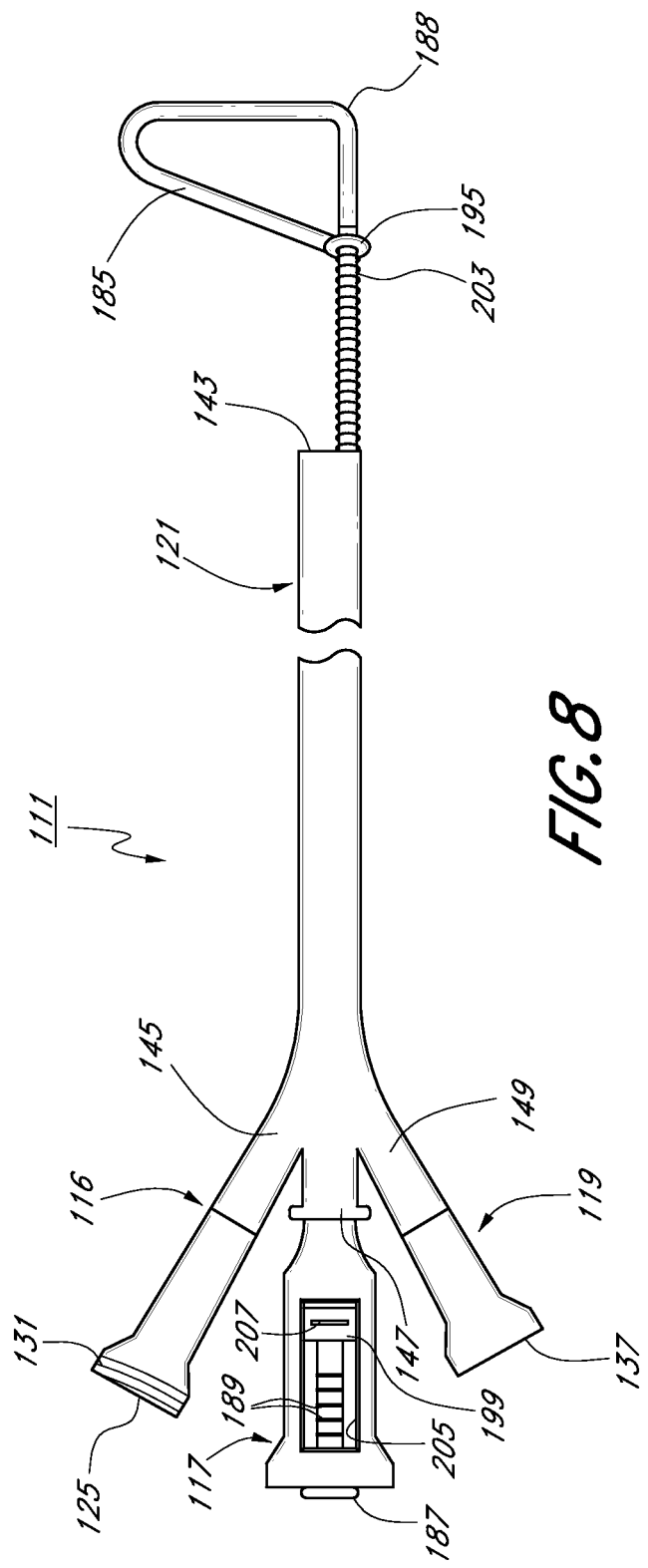
FIG. 8 is a plan view of the system shown in FIG. 6, with the mechanical expansion structure shown in an advanced and expanded state.
Figure 9:
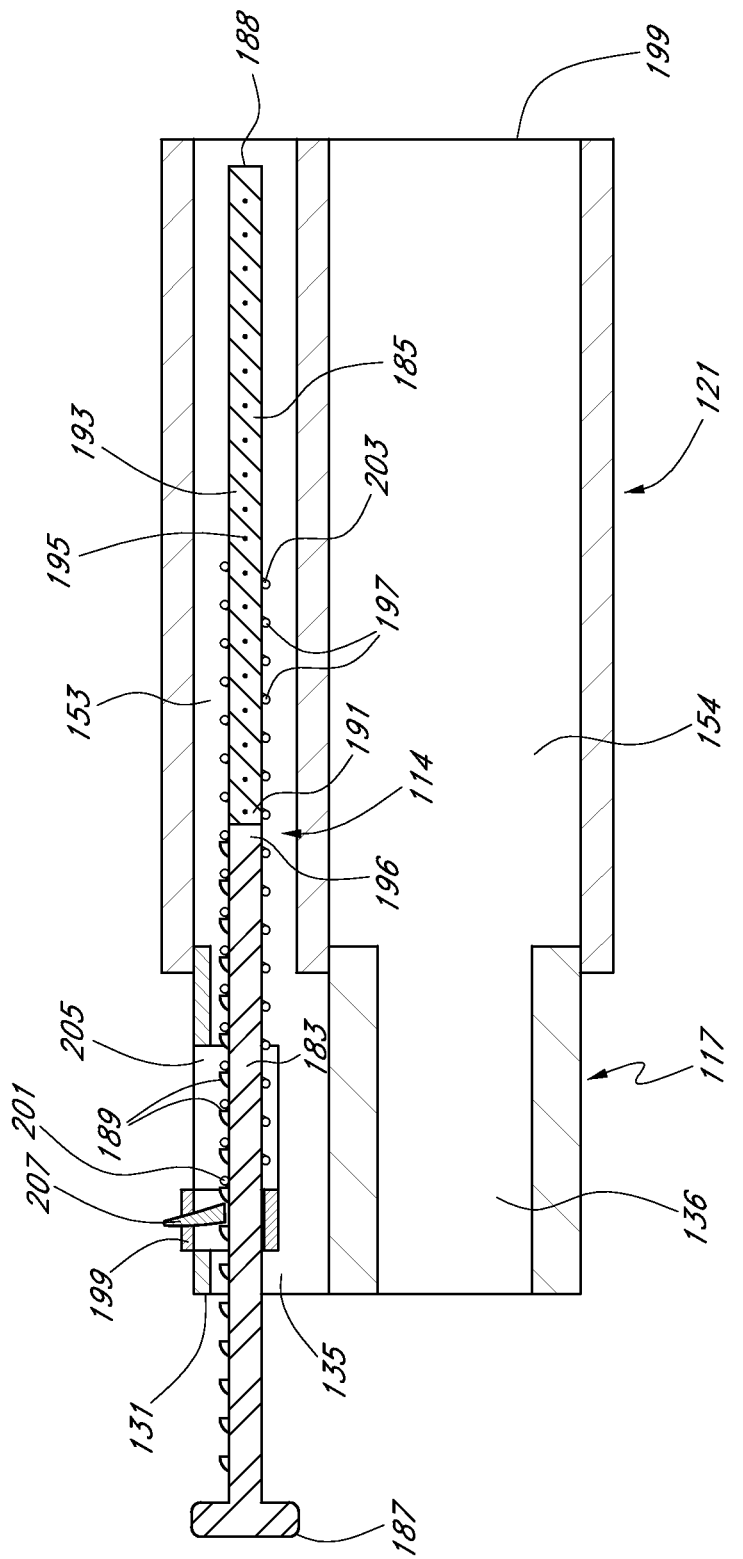
FIG. 9 is a longitudinal section view of the system shown in FIG. 6, with the mechanical expansion structure shown in a retracted and non-expanded state.

Thus, the embodiment of FIGS. 7 and 8 can be modified such that two or three or four or more axially extending ribs are advanceable from a generally axially extending configuration such as that illustrated in FIG. 7 to a radially outwardly inclined configuration such as that illustrated in FIG. 8.

In an alternate embodiment (not illustrated), a plurality of axially extending ribs are connected together at a distal end to a pull wire which extends to the proximal end of the instrument. The proximal ends of the ribs are connected to a tubular column strength support having a central lumen through which the pull wire extends. Proximal retraction of the pull wire axially shortens the distension element while simultaneously radially expanding the ribs to the second, radially enlarged configuration to produce a cage having a three dimensional volume.

Both the endoscope and the tissue cutting element may be provided in a steerable configuration, such that they may be distally advanced into the working space created by the distension element and laterally deflected which, in combination with axial rotation, gives access to a wide variety of treatment sites within the distension structure. Any of a wide variety of deflection mechanisms may be utilized, as are well understood in the art, including axially extending pull wires and push wires mechanically linked to a proximal control such as a rotatable knob or slider switch.

In any of the foregoing embodiments, the expansion structure may be utilized both to accomplish initial expansion as well as retention of the tissue in the expanded configuration. Alternatively, fluid pressure such as water pressure as has been used conventionally may be utilized to achieve tissue expansion, and the expansion structures of the present invention may be utilized to retain the tissue in the expanded configuration. At that point, the fluid pressure may be reduced, such that the risk of intravasation is thereby eliminated.

The embodiments of the present invention described above are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A method of performing a medical procedure, said method comprising the steps of:
   a) using a mechanical expansion structure to maintain a uterus in a distended state equivalent to that achieved by introduction of a liquid distension media at a pressure of at least 40 mm Hg; and
   b) performing at least one of examining and treating tissue located within the distended uterus.

2. The method as claimed in claim 1 further comprising, prior to the maintaining step, distending the uterus with a fluid.

3. The method as claimed in claim 1 wherein said step of examining tissue within the distended uterus comprises visualizing the tissue using a transcervically placed hysteroscope.

4. The method as claimed in claim 1 wherein said step of treating tissue comprises cutting tissue.

5. The method as claimed in claim 1 further comprising, prior to said maintaining step, transcervically inserting an introducer into the uterus.

6. The method as claimed in claim 5 further comprising, after said step of transcervically inserting the introducer into the uterus and prior to said maintaining step, the step of delivering the mechanical expansion structure to the uterus through the introducer.

7. The method as claimed in claim 5 further comprising, after said step of transcervically inserting the introducer into the uterus and prior to said maintaining step, the step of delivering the mechanical expansion structure to the uterus outside of the introducer.

8. The method as claimed in claim 1 further comprising, after the maintaining step, the step of transcervically inserting an introducer into the uterus.

9. A method of performing a medical procedure, said method comprising the steps of:
   a) inserting an introducer into a body to an internal site, the introducer including a visualization lumen and an instrument lumen;
   b) delivering a visualization device to the internal site through the visualization lumen;
   c) delivering a mechanical expansion structure to the internal site;
   d) deploying the mechanical expansion structure to distend the internal site;
   e) observing the distended internal site using the visualization device;
   f) after delivering the mechanical expansion structure, delivering a tissue modifying device to the internal site through the instrument lumen; and
   g) modifying tissue at the internal site using the tissue modifying device.

10. The method as claimed in claim 9 wherein the internal site is within the uterus.

11. The method as claimed in claim 9 wherein the mechanical expansion structure is delivered to the internal site outside of the introducer.

12. The method as claimed in claim 9 wherein the introducer further includes a distension lumen and wherein the mechanical expansion structure is delivered to the internal site through the distension lumen.

13. The method as claimed in claim 9 wherein the mechanical expansion structure is delivered to the internal site through the instrument lumen.

14. The method as claimed in claim 9 wherein the introducer further includes a fluid lumen, the method further comprising the step of delivering a fluid to the internal site through the fluid lumen.

15. The method as claimed in claim 9 wherein the mechanical expansion structure delivery and deployment steps are performed prior to the introducer delivery step.

* * * * *